(12) United States Patent
Amano et al.

(10) Patent No.: US 6,515,134 B1
(45) Date of Patent: Feb. 4, 2003

(54) SUBSTITUTED ACETYLPRIDINE DERIVATIVES AND PROCESS FOR THE PREPARATION OF INTERMEDIATES FOR OPTICALLY ACTIVE BETA-3 AGONIST BY THE USE OF THE SAME

(75) Inventors: Susumu Amano, Hyogo (JP); Naoaki Taoka, Hyogo (JP); Masaru Mitsuda, Hyogo (JP); Kenji Inoue, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/926,021

(22) PCT Filed: Feb. 16, 2000

(86) PCT No.: PCT/JP00/00861
§ 371 (c)(1),
(2), (4) Date: Nov. 7, 2001

(87) PCT Pub. No.: WO00/48997
PCT Pub. Date: Aug. 24, 2000

(30) Foreign Application Priority Data

Feb. 16, 1999 (JP) .............................. 11-037766
Dec. 9, 1999 (JP) ........................... 11-350801

(51) Int. Cl.$^7$ ...................... C07D 213/26; C07D 213/30
(52) U.S. Cl. ...................... 546/315; 546/290; 546/340; 514/345; 514/354
(58) Field of Search ................. 546/290, 340, 546/315; 514/354, 345

(56) References Cited

U.S. PATENT DOCUMENTS

| | | | | |
|---|---|---|---|---|
| 3,871,958 A | * | 3/1975 | Nakazawa et al. | 435/106 |
| 4,963,492 A | * | 10/1990 | Keller et al. | 435/155 |
| 5,541,197 A | * | 7/1996 | Fisher et al. | 514/311 |
| 5,559,256 A | * | 9/1996 | Gordon et al. | 552/303 |
| 5,714,506 A | * | 2/1998 | Fisher et al. | 514/352 |
| 5,792,871 A | * | 8/1998 | Chartrain et al. | 435/122 |
| 5,846,791 A | * | 12/1998 | Chartrain et al. | 435/122 |
| 6,001,856 A | * | 12/1999 | Dow | 514/312 |

FOREIGN PATENT DOCUMENTS

| | | | |
|---|---|---|---|
| EP | WO 98/03672 | | 1/1998 |
| EP | 0 842 924 A1 | | 5/1998 |
| EP | 920864 | * | 6/1999 |
| EP | 994105 | * | 4/2000 |
| GB | 1266430 | * | 3/1972 |
| WO | 91/09856 | * | 7/1991 |
| WO | 97/16189 | * | 5/1997 |
| WO | 98/21184 | * | 5/1998 |

OTHER PUBLICATIONS

Chung, J. Y. et al. "Practical chemoenzymatic synthesis of a 3–pyridylethanolamino β$_3$ adrenergic receptor agonist" Tetrahedron Letters 40 (1999), 6739–6743.

* cited by examiner

Primary Examiner—Alan L. Rotman
Assistant Examiner—Rita Desai
(74) Attorney, Agent, or Firm—Armstrong, Westerman & Hattori, LLP

(57) ABSTRACT

It is an objective to produce intermediates of optically active beta-3 adrenaline receptor agonists from readily available raw materials in a safe, efficient and industrially advantageous manner. A substituted acetylpyridine derivative represented by the general formula (9) is reduced by enantioselective reduction to produce an optically active hydroxyethyl derivative represented by the general formula (10) (wherein * represents an asymmetric carbon atom), and it is further derivatized to an intermediate of an optically active beta-3 adrenaline receptor agonist, such as an optically active dihydroxyethylpyridine derivative represented by the general formula (14) or an optically active oxirane derivative represented by the general formula (16).

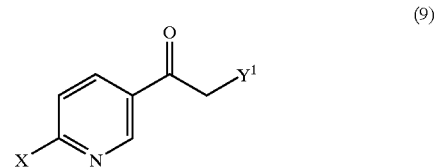

(9)

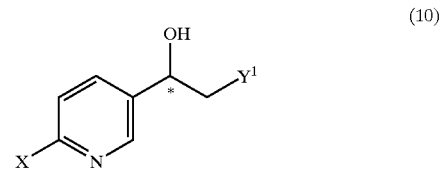

(10)

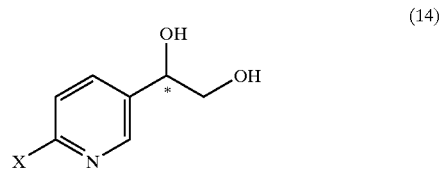

(14)

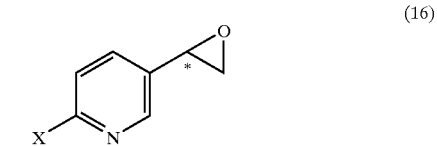

(16)

8 Claims, No Drawings

SUBSTITUTED ACETYLPRIDINE DERIVATIVES AND PROCESS FOR THE PREPARATION OF INTERMEDIATES FOR OPTICALLY ACTIVE BETA-3 AGONIST BY THE USE OF THE SAME

CROSS-REFERENCE

This application is a 371 of PCT/JP00/00861 filed Feb. 16, 2000

TECHNICAL FIELD

The present invention relates to a method of producing optically active beta-3 adrenaline receptor agonist intermediates which are important in producing medicinals, and to those important intermediates.

BACKGROUND ART

Known in the art for the production of optically active dihydroxyethylpyridine derivatives or optically active oxirane derivatives which are intermediates of optically active beta-3 adrenaline receptor agonists and are represented by the general formula (14):

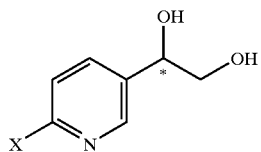

(14)

in the formula, X represents a hydrogen, a halogen, an acyloxy group containing 1 to 10 carbon atoms, an alkoxy group containing 1 to 10 carbon atoms, an amino group or a substituted amino group; or by the general formula (16):

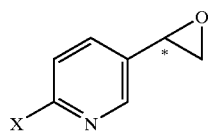

(16)

in the formula, X is as defined above, are:
  (i) the process which involves the catalytic asymmetric dihydroxylation reaction of vinylpyridine derivatives (WO9821184),
  (ii) the process which involves the asymmetric reduction of halo acetylpyridine derivatives with diisopinocamphenylborane chloride (U.S. Pat. No. 556142, U.S. Pat. No. 5714506), and (iii) the process which involves the asymmetric reduction of aminoacetylpyridine derivatives using a microorganism (WO9803672).

However, the process (i) uses highly toxic osmium oxide and further requires an expensive asymmetric ligand, hence have problems from the industrial utilization viewpoint.

The process (ii) requires the use of a stoichiometric amount of diisopinocamphenylborane chloride, which is an expensive asymmetric reducing agent, hence has a problem from the commercial viewpoint. Further, the halo acetylpyridine derivative unsubstituted or substituted by chlorine in position 2, which is used as the substrate for asymmetric reduction, is produced by halogenation of the methyl group of the corresponding methyl ketone. However, the methyl ketone is difficult to obtain and it is necessary to synthesize the same using diazomethane, which is difficult to handle on an industrial scale because of its toxicity and explosiveness.

The process (iii) is only applicable to derivatives having no substituent on the pyridine ring [namely compounds of the general formula (7) or (9) shown below in which X is a hydrogen] and there is no disclosure about the method of producing pyridine derivatives substituted in position 2 such as 2-amino pyridine derivatives.

Those substituted acetylpyridine derivatives substituted by an amino group in position 2 which are represented by the general formula (1):

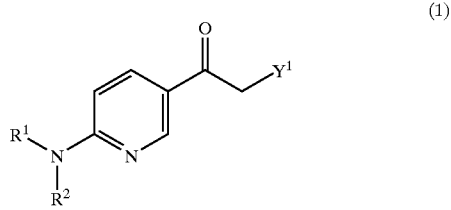

(1)

in the formula, $R_1$ and $R^2$ each independently represents a hydrogen, an alkyl group containing 1 to 10 carbon atoms, an aralkyl group containing 1 to 10 carbon atoms, an acyl group containing 1 to 10 carbon atoms, or an alkyloxycarbonyl group containing 1 to 10 carbon atoms and $Y^1$ represents a halogen, a hydroxyl group, an acyloxy group containing 1 to 10 carbon atoms, a sulfonyloxy group containing 1 to 10 carbon atoms, an alkoxy group containing 1 to 10 carbon atoms, an amino group, an alkylamino group containing 1 to 15 carbon atoms, an aralkyl amino group containing 1 to 15 carbon atoms, a sulfanyl group, an alkyl sulfanyl group containing 1 to 10 carbon atoms, or an aralkyl sulfanyl group containing 1 to 10 carbon atoms, are expected to be important compounds in the production of intermediates of optically active beta-3 adrenaline receptor agonists. However, they are unknown in the literature.

Those pivaloyloxyacetylpyridine derivatives represented by the general formula (2):

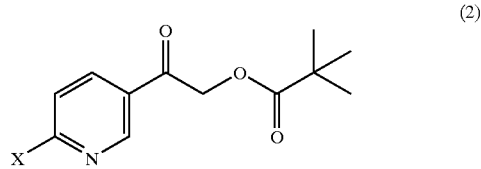

(2)

in the formula, X represents a hydrogen, a halogen, a hydroxyl group, an acyloxy group containing 1 to 10 carbon atoms, an alkoxy group containing 1 to 10 carbon atoms, an amino group or a substituted amino group, are also expected to be important compounds in the production of intermediates of optically active beta-3 adrenaline receptor agonists. They are, however, unknown in the literature.

Further, those optically active pivaloyloxy-hydroxyethyl derivatives represented by the general formula (3):

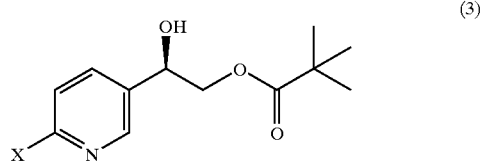

(3)

in the formula, X represents a hydrogen, a halogen, a hydroxyl group, an acyloxy group containing 1 to 10 carbon atoms, an alkoxy group containing 1 to 10 carbon atoms, an amino group or a substituted amino group, are also expected to be important compounds in the production of intermediates of optically active beta-3 adrenaline receptor agonists. They are, however, unknown in the literature.

Furthermore, those optically active dihydroxyethylpyridine derivatives represented by the formula (4):

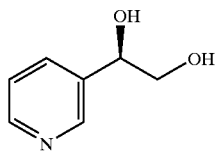

(4)

or a salt thereof is also expected to be an important compound in the production of intermediates of optically active beta-3 adrenaline receptor agonists. It is, however, unknown in the literature.

SUMMARY OF INVENTION

In view of the current state of the art as mentioned above, it is an object of the invention to produce an optically active dihydroxyethylpyridine derivative and an optically active oxirane derivative, which is an important intermediate in producing an optically active beta-3 adrenaline receptor agonist (as described, for example, in WO9821184 and U.S. Pat. No. 5,561,142) represented by the following general formula (17):

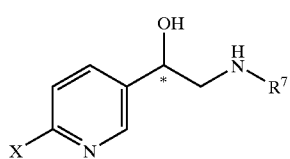

(17)

which can readily be converted to the above-mentioned compounds (17) by expedient methods known in the art, from readily available raw materials in a safe and efficient manner and, further, in an industrially advantageous manner.

Thus, the present invention provides a substituted acetylpyridine derivative substituted by an amino group in position 2 which is represented by the general formula (1):

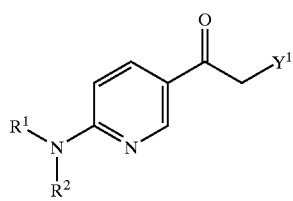

(1)

in the formula, $R_1$ and $R^2$ each independently represents a hydrogen, an alkyl group containing 1 to 10 carbon atoms, an aralkyl group containing 1 to 10 carbon atoms, an acyl group containing 1 to 10 carbon atoms or an alkyloxycarbonyl group containing 1 to 10 carbon atoms and Y1 represents a halogen, a hydroxyl group, an acyloxy group containing 1 to 10 carbon atoms, a sulfonyloxy group containing 1 to 10 carbon atoms, an alkoxy group containing 1 to 10 carbon atoms, an amino group, an alkylamino group containing 1 to 15 carbon atoms, an aralkyl amino group containing 1 to 15 carbon atoms, a sulfanyl group, an alkyl sulfanyl group containing 1 to 10 carbon atoms or an aralkyl sulfanyl group containing 1 to 10 carbon atoms.

The invention further provides a pivaloyloxyacetylpyridine derivative represented by the general formula (2):

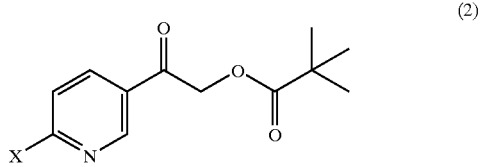

(2)

in the formula, X represents a hydrogen, a halogen, or a hydroxyl group, an acyloxy group containing 1 to 10 carbon atoms, an alkoxy group containing 1 to 10 carbon atoms, an amino group or a substituted amino group.

The invention further provides an optically active pivaloyloxyhydroxyethylpyridine derivative represented by the general formula (3):

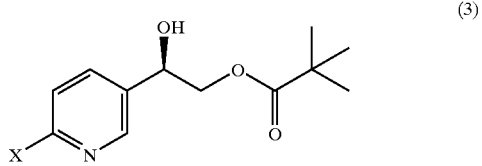

(3)

in the formula, X represents a hydrogen, a halogen, a hydroxyl group, an acyloxy group containing 1 to 10 carbon atoms, an alkoxy group containing 1 to 10 carbon atoms, an amino group or a substituted amino group.

The invention also provides an optically active dihydroxyethylpyridine derivative represented by the formula (4):

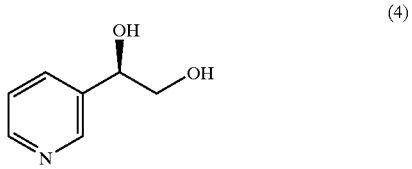

(4)

or a salt thereof.

The invention further provides a production method of a substituted acetylpyridine derivative represented by the general formula (7):

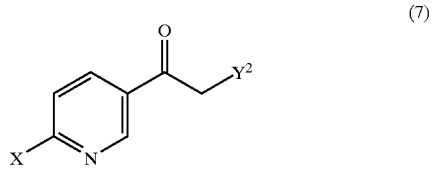

(7)

in the formula, $Y^2$ represents a halogen and X represents a hydrogen, a halogen, a hydroxyl group, an acyloxy group containing 1 to 10 carbon atoms, an alkoxy group containing 1 to 10 carbon atoms, an amino group or a substituted amino group, which comprises reacting, with a base, a haloacetic acid derivative represented by the general formula (5):

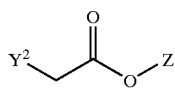
(5)

in the formula, $Y^2$ is as defined above and Z represents a hydrogen, an alkali metal, a halogenated alkaline earth metal or a silyl group containing 1 to 10 carbon atoms, to prepare an enolate, reacting the same with a substituted nicotinic acid ester represented by the general formula (6):

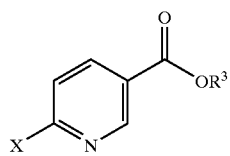
(6)

in the formula, X is as defined above and $R^3$ represents an alkyl group containing 1 to 10 carbon atoms or an aralkyl group containing 1 to 10 carbon atoms, and then subjecting the reaction product to acid treatment.

The invention further provides a production method of an optically active hydroxyethyl derivative represented by the general formula (10):

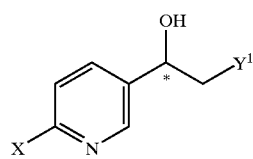
(10)

in the formula, X represents a hydrogen, a halogen, a hydroxyl group, an acyloxy group containing 1 to 10 carbon atoms, an alkoxy group containing 1 to 10 carbon atoms, an amino group or a substituted amino group, $Y^1$ represents a halogen atom or a hydroxyl group, an acyloxy group containing 1 to 10 carbon atoms, a sulfonyloxy group containing 1 to 10 carbon atoms, an alkoxy group containing 1 to 10 carbon atoms, an amino group, an alkylamino group containing 1 to 15 carbon atoms, anaralkylamino group containing 1 to 15 carbon atoms, a sulfanyl group, an alkyl sulfanyl group containing 1 to 10 carbon atoms or an aralkyl sulfanyl group containing 1 to 10 carbon atoms and * represents an asymmetric carbon atom, which comprises enantioselectively reducing a substituted acetylpyridine derivative represented by the general formula (9):

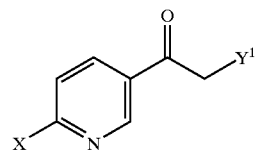
(9)

in the formula, X and $Y^1$ are as defined above.

The invention further provides a production method of a substituted acetylpyridine derivative represented by the general formula (12):

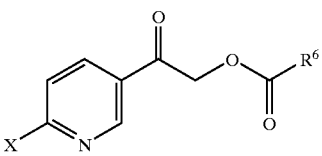
(12)

in the formula, X is as defined above and $R^6$ represents an alkyl group containing 1 to 15 carbon atoms, anaralkyl group containing 1 to 15 carbon atoms or an aryl group containing 6 to 16 carbon atoms, which comprises reacting a substituted acetylpyridine derivative represented by the above general formula (7) with a carboxylic acid represented by the general formula (11):

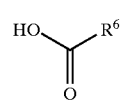
(11)

in the formula, $R^6$ is as defined above, in the presence of a base and a quaternary ammonium salt.

The invention further provides a production method of an optically active acyloxyhydroxyethylpyridine derivative represented by the general formula (13):

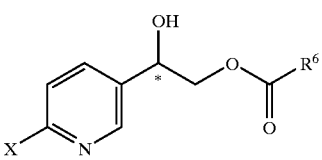
(13)

in the formula, X represents a hydrogen, a halogen, a hydroxyl group, an acyloxy group containing 1 to 10 carbon atoms, an alkoxy group containing 1 to 10 carbon atoms, an amino group or a substituted amino group, $R^6$ represents an alkyl group containing 1 to 15 carbon atoms, an aralkyl group containing 1 to 15 carbon atoms or an aryl group containing 6 to 16 carbon atoms and * represents an asymmetric carbon atom, which comprises enantioselectively reducing a substituted acetylpyridine derivative represented by the above general formula (12).

The invention further provides a production method of an optically active dihydroxyethylpyridine derivative represented by the general formula (14):

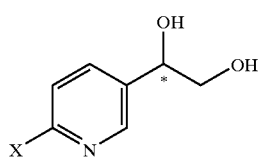
(14)

in the formula, X is as defined above and * represents an asymmetric carbon atom, which comprises subjecting an optically active acyloxyhydroxyethylpyridine derivative represented by the above general formula (13) to solvolys is in a lower alcohol solvent in the presence of a quaternary ammonium hydroxide.

The invention still further provides a production method of an optically active hydroxyethyl derivative represented by the general formula (15):

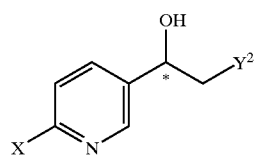

(15)

in the formula, $Y^2$ and X are as defined above and * represents an asymmetric carbon atom,
which comprises reacting, with a base, a haloacetic acid derivative represented by the above general formula (5) to prepare an enolate,
reacting the same with a substituted nicotinic acid ester represented by the above general formula (6),
subjecting the reaction product to acid treatment to prepare a substituted acetylpyridine derivative represented by the above general formula (7), followed by enantioselective reduction.

The invention still further provides a production method of an optically active oxirane derivative represented by the general formula (16):

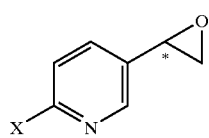

(16)

in the formula, X is as defined above and * represents an asymmetric carbon atom,
which comprises reacting, with a base, a haloacetic acid derivative represented by the above general formula (5) to prepare an enolate,
reacting the same with a substituted nicotinic acid ester represented by the above general formula (6), subjecting the reaction product to acid treatment to prepare a substituted acetylpyridine derivative represented by the above general formula (7), subjecting this to enantioselective reduction to prepare an optically active hydroxyethyl derivative represented by the above general formula (15), followed by treating it with a base.

The invention still further provides a production method of an optically active dihydroxyethylpyridine derivative represented by the above general formula (14)
which comprises reacting a substituted acetylpyridine derivative represented by the above general formula (7) with a carboxylic acid represented by the above general formula (11) in the presence of a base and a quaternary ammonium salt to prepare a substituted acetylpyridine derivative represented by the above general formula (12) and subjecting this to enantioselective reduction to prepare an optically active acyloxyhydroxyethyl-pyridine derivative represented by the above general formula (13), followed by subjecting it to solvolysis.

The invention still further provides a production method of an optically active dihydroxyethylpyridine derivative represented by the above general formula (14)
which comprises subjecting a substituted acetylpyridine derivative represented by the above general formula (12) to solvolysis while enantioselectively reducing in the presence of a base to thereby directly obtain the optically active dihydroxyethylpyridine derivative represented by the above general formula (14).

In the following, the invention is described in detail.

DETAILED DISCLOSURE OF THE INVENTION

By employing the processes of the invention, it is possible to produce optically active oxirane derivatives represented by the general formula (16) as well as optically active dihydroxyethylpyridine derivatives represented by the general formula (14). Basically, the processes can be outlined by the reaction schemes shown below. The process for producing the optically active oxirane derivatives comprises three steps, namely (a) the step of converting a substituted nicotinic acid ester represented by the general formula (6) to a substituted acetylpyridine derivative represented by the general formula (7), (b) the step of reducing the latter to a corresponding optically active hydroxyethyl derivative represented by the general formula (15) and (c) the step of further treating the same with a base to derivatize the same into a corresponding optically active oxirane derivative.

On the other hand, the process for producing the optically active dihydroxyethylpyridine derivatives comprises four steps, namely (a) the step of converting a substituted nicotinic acid ester represented by the general formula (6) to a substituted acetylpyridine derivative represented by the general formula (7), as mentioned above, (d) the step of converting the latter to a substituted acetylpyridine derivative having an acyloxy substituent as represented by the general formula (12), (b) the step of reducing the same to a corresponding optically active hydroxyethyl derivative represented by the general formula (13), as mentioned above, and (e) the step of further derivatizing the same into a corresponding optically active dihydroxyethylpyridine derivative by solvolysis of the acyloxy group. In the following, these steps (a) to (e) are described in detail one by one.

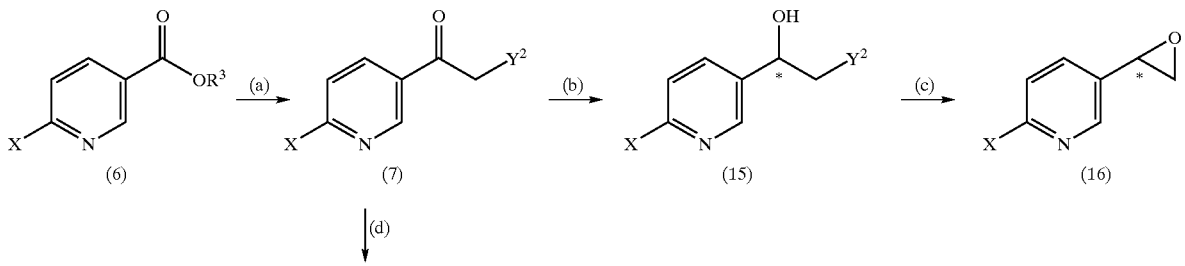

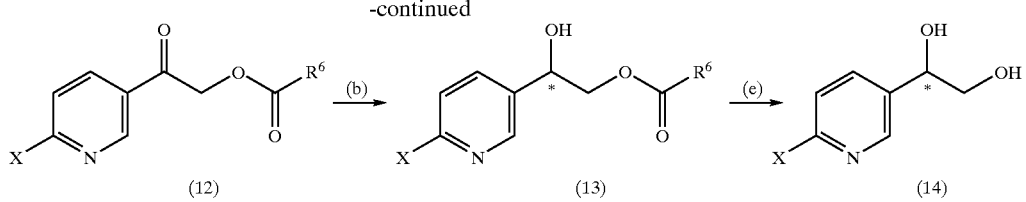

1. Step (a)

This step (a) comprises reacting, with a base, a haloacetic acid derivative represented by the above general formula (5) to prepare an enolate, reacting the same with a substituted nicotinic acid ester represented by the above general formula (6) and subjecting the reaction product to acid treatment to thereby prepare a substituted acetylpyridine derivative represented by the above general formula (7).

In the general formula (5) or (7), $Y^2$ represents a halogen. Specifically, there may be mentioned fluorine, chlorine, bromine, iodine, etc. Chlorine or bromine is preferred and chlorine is more preferred.

In the general formula (5), Z represents hydrogen, an alkali metal, halogenated alkaline earth metal oral silyl group containing 1 to 10 carbon atoms. Specifically, Z includes, but is not limited to, hydrogen, lithium, sodium, potassium, magnesium chloride, magnesium bromide, calcium chloride, trimethylsilyl, tert-butyldimethylsilyl, phenyldimethylsilyl and the like. Preferred is sodium or magnesium chloride.

Preferred as the haloacetic acid derivative represented by the general formula (5) are sodium chloroacetate, sodium bromoacetate, magnesium chloroacetate chloride and magnesium bromoacetate bromide. Magnesium chloroacetate chloride prepared in situ in advance by mixing sodium chloroacetate with magnesium chloride and allowing sodium chloride to precipitate out may also be used.

The use amount of haloacetic acid derivative represented by the general formula (5) is 1 to 10 molar equivalents, preferably 1 to 3 molar equivalents, relative to the substituted nicotinic acid ester represented by the general formula (6).

The base to be used in preparing an enolate from haloacetic acid derivative represented by the general formula (5) is not particularly restricted but includes, among others, metal amides such as lithium amide, sodium amide, lithium diisopropylamide, magnesium diisopropylamide chloride, magnesium diisopropylamide bromide and magnesium dicyclohexylamide chloride; alkylmetals such as methyllithium, n-butyllithium, methylmagnesium bromide, i-propylmagnesium chloride and tert-butylmagnesium chloride; metal alkoxides such as sodium methoxide, magnesium ethoxide and potassium tert-butoxide; and metal hydrides such as lithium hydride, sodium hydride, potassium hydride and calcium hydride. Preferred among them are magnesium amides represented by the general formula (8):

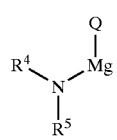

(8)

In general formula (8), $R^4$ and $R^5$ each independently represents an alkyl group containing 1 to 10 carbon atoms or a silyl group containing 1 to 10 carbon atoms. $R^4$ and $R^5$ may be the same or different. Specifically, they include, but are not limited to, methyl, ethyl, i-propyl, tert-butyl, n-octyl, trimethylsilyl, triethylsilyl, phenyldimethylsilyl and the like. Preferably, $R^4$ and $R^5$ each represents an isopropyl group. Q represents a halogen. Chlorine, bromine or iodine is preferred and chlorine is more preferred.

The magnesium amide represented by the general formula (8) can readily be prepared by a method known in the art (e.g. the method described in Japanese Kokai Publication Hei-8-523420) from an inexpensive and readily available secondary amine and a Grignard reagent.

The use amount of such base is 1 to 10 molar equivalents, preferably 2 to 6 molar equivalents, relative to the substituted nicotinic acid ester represented by the general formula (6).

In the above general formula (6) or (7), X represents a hydrogen, a halogen, a hydroxyl group, an acyloxy group containing 1 to 10 carbon atoms, an alkoxy group containing 1 to 10 carbon atoms, an amino group or a substituted amino group. Specifically, it includes, but is not limited to, hydrogen, fluorine, chlorine, bromine, iodine, hydroxyl, acetyloxy, benzoyloxy, methoxy, butoxy, benzyloxy, amino, acetylamino, benzoylamino, phthaloylamino, dimethylamino, dibenzylamino, benzyloxycarbonylamino, tert-butyloxycarbonylamino, ethoxycarbonylamino and the like.

Preferred among them are hydrogen, halogens such as chlorine, bromine and iodine, hydroxyl, amino or substituted amino groups such as acetylamino, benzoylamino, phthaloylamino, dimethylamino, dibenzylamino, benzyloxycarbonylamino, tert-butyloxycarbonylamino and ethoxycarbonylamino. More preferred are hydrogen, chlorine, amino and substituted amino groups such as acetylamino. Particularly preferred are hydrogen, chlorine and acetylamino.

In the general formula (6), $R^3$ represents an alkyl group containing 1 to 10 carbon atoms or an aralkyl group containing 1 to 10 carbon atoms. Specifically, it includes, but is not limited to, methyl, ethyl, tert-butyl, phenyl, benzyl, p-methoxybenzyl and the like. Preferred dare lower alkyl groups such as methyl and ethyl.

In the step (a), the order of mixing of the haloacetic acid derivative, base and substituted nicotinic acid ester is optional. For example, the enolate preparation and the reaction of the enolate with the substituted nicotinic acid ester can be carried out at once by adding dropwise a base to a mixed solution containing the substituted nicotinic acid ester and haloacetic acid derivative.

An aprotic organic solvent is preferably used as the reaction solvent in the step (a). The aprotic organic solvent is not particularly restricted but includes, among others, hydrocarbon solvents such as benzene, toluene, n-hexane and cyclohexane; ether solvents such as diethyl ether, tetrahydrofuran (THF), 1,4-dioxane, methyl tert-butyl ether, dimethoxyethane and ethylene glycol dimethyl ether; halogenated solvents such as methylene chloride, chloroform and 1,1,1-trichloroethane; and aprotic polar solvents such as dimethylformamide, N-methylpyrrolidone and hexamethylphosphoric triamide. These may be used singly or two or more of them may be used in combination. Preferred are hydrocarbon solvents such as benzene, toluene, n-hexane and cyclohexane; and ether solvents such as diethyl ether, tetrahydrofuran, 1,4-dioxane, methyl tert-butyl ether, dimethoxyethane and diethylene glycol dimethyl ether.

The reaction temperature is preferably −80° C. to 100° C., more preferably −20° C. to 60° C.

The acid to be used in the acid treatment in this step (a) may be any of general inorganic or organic acids, for example hydrochloric acid, sulfuric acid, nitric acid, acetic acid and citric acid.

This acid treatment can be effected by mixing a sufficient amount of the acid to neutralize the base with the reaction mixture at 0° C. to around room temperature and stirring the mixture for about several minutes to several hours.

For isolating the product from the reaction mixture in this step (a) after completion of the series of reactions, the reaction mixture is subjected to after-treatment in the conventional manner. For example, after acid treatment, an extraction procedure is performed using an ordinary extraction solvent such as ethyl acetate, diethyl ether, methylene chloride, toluene or hexane. Removal of the reaction solvent and extraction solvent from the extract thus obtained by a procedure such as heating under reduced pressure, whereupon the desired product is obtained. Although the thus-obtained desired product is almost pure, the purity thereof may further be raised by conventional means of purification, such as purification by crystallization, fractional distillation or column chromatography.

2. Step (b)

The step (b) comprises enantioselectively reducing a substituted acetylpyridine derivative represented by the above general formula (9) to prepare an optically active hydroxyethyl derivative represented by the above general formula (10).

The substrate to be reduced in the enantioselective reduction according to the present invention is a substituted acetylpyridine derivative represented by the general formula (9):

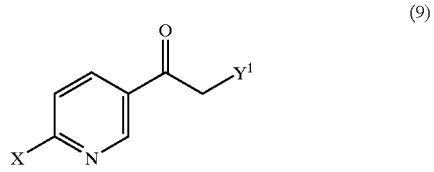

(9)

In the general formula (9), X represents a hydrogen, a halogen, a hydroxyl group, an acyloxy group containing 1 to 10 carbon atoms, an alkoxy group containing 1 to 10 carbon atoms, an amino group or a substituted amino group. Specifically, it includes, but is not limited to, hydrogen, fluorine, chlorine, bromine, iodine, hydroxyl, acetyloxy, benzoyloxy, methoxy, butoxy, benzyloxy, amino, acetylamino, benzoylamino, phthaloylamino, dimethylamino, dibenzylamino, benzyloxycarbonylamino, tert-butyloxycarbonylamino and ethoxycarbonylamino.

Preferred among them are hydrogen, halogens such as chlorine, bromine and iodine, hydroxyl, amino or substituted amino groups such as acetylamino, benzoylamino, phthaloylamino, dimethylamino, dibenzylamino, benzyloxycarbonylamino, tert-butyloxycarbonylamino, ethoxycarbonylamino and the like. More preferred are hydrogen, chlorine, amino and substituted amino groups such as acetylamino. In particular, hydrogen, chlorine and acetylamino are preferred.

In the general formula (9), $Y^1$ represents a halogen, a hydroxyl group, an acyloxy group containing 1 to 10 carbon atoms, a sulfonyloxy group containing 1 to 10 carbon atoms, an alkoxy group containing 1 to 10 carbon atoms, an amino group, an alkylamino group containing 1 to 15 carbon atoms, an aralkyl amino group containing 1 to 15 carbon atoms, a sulfanyl group, an alkylsulfanyl group containing 1 to 10 carbon atoms or an aralkylsulfanyl group containing 1 to 10 carbon atoms. Specifically, it includes, but is not limited to, hydrogen, fluorine, chlorine, bromine, iodine, hydroxyl, acetyloxy, benzoyloxy, trifluoroacetyloxy, methanesulfonyloxy, benzenesulfonyloxy, toluenesulfonyloxy, methoxy, tert-butyloxy, benzyloxy, amino, dimethylamino, ethylamino, phenylethylamino, p-nitrophenylethylamino, phenoxyethylamino and the like.

Preferred among them are halogens such as chlorine, bromine and iodine; hydroxyl; acyloxy groups such as acetyloxy and benzoyloxy; and sulfonyloxy groups such as methanesulfonyloxy, benzenesulfonyloxy and to luenesulfonyloxy. More preferred are halogens, a hydroxyl group and an acyloxy group containing 1 to 10 carbon atoms. Among the halogens, chlorine is preferred.

Those substituted acetylpyridine derivatives [general formula (7)] in which $Y^1$ in general formula (9) is a halogen atom can be used as obtained in the above step (a). Those substituted acetylpyridine derivatives in which $Y^1$ in general formula (9) is a halogen atom can be derived from those represented by the general formula (7) using a method known in the art. For example, when a substituted acetylpyridine derivative represented by the general formula (7) is reacted with an alkoxy anion, acyloxy anion or alkylsulfanyl anion, then a substituted acetylpyridine derivative in which $Y^1$ is an alkoxy, acyloxy or alkyl sulfanyl group, respectively, is obtained. Further, hydrolysis of a substituted acetylpyridine derivative thus substituted by an acyloxy group, for instance, gives the corresponding substituted acetylpyridine derivative in which $Y^1$ is a hydroxyl group.

In particular, those substituted acetylpyridine derivatives in which $Y^1$ is an acyloxy group, namely the substituted acetylpyridine derivatives represented by the general formula (12):

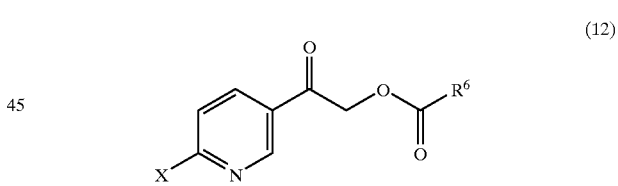

(12)

can be derived from substituted acetylpyridine derivatives of general formula (7) by a novel method to be described later herein.

In the general formula (12), X is as defined above. $R^6$ represents an alkyl group containing 1 to 15 carbon atoms, an aralkyl group containing 1 to 15 carbon atoms or an aryl group containing 6 to 16 carbon atoms. Specifically, it includes, but is not limited to, methyl, ethyl, n-propyl, i-propyl, n-butyl, i-butyl, tert-butyl, n-octyl, benzyl, anisyl, p-nitrobenzyl, phenyl, p-tolyl, naphthyl and the like. Methyl, ethyl, n-propyl, i-propyl, n-butyl, tert-butyl andphenyl are preferred and methyl, tert-butyl and phenyl are more preferred. Still more preferred is tert-butyl.

The enantioselective reduction in step (b) is an asymmetric reduction carried out by a biological or chemical technique. As the biological asymmetric reduction technique, there may be mentioned asymmetric reduction by means of a microorganism or a reducing enzyme derived therefrom.

As the chemical asymmetric reduction technique, there may be mentioned hydrogen transfer type reduction using a catalyst prepared from a ruthenium complex, an optically active amine and a base; asymmetric hydrogenation using an asymmetric catalyst composed of rhodium, ruthenium, iridium or palladium and a chiral phosphine ligand; and borane reduction using, as an asymmetric ligand, an amino alcohol derived from an optically active alpha-amino acid; among others. Among them, the reduction using a microorganism and the hydrogen transfer type reduction are preferred.

When a microorganism is used for the enantioselective reduction, the substrate substituted acetylpyridine derivative is reduced (R)-selectively and thus the corresponding (R)-hydroxyethyl derivative can be obtained preferentially. In this case, the reduction reaction can be carried out using a microorganism-derived carbonyl reducing enzyme or a culture of a microorganism having an ability of producing said carbonyl reducing enzyme or a treatment product thereof.

Usable as the carbonyl reducing enzyme-producing microorganism in the R-selective reduction are microorganisms belonging to the genera Ashbya, Candida, Cryptococcus, Debaryomyces, Guilliermondella, Hansenula, Metschnikowia, Pichia, Rhodotorula, Rhodosporidium, Saccharomycopsis, Schwanniomyces, Sporidiobolus, Sporobolomyces, Torulaspora and Yarrowia. Specifically, use can be made of *Ashbya gossypii, Candida catinulata, Candida fructus, Candida galacta, Candida gropengiesseri, Candida guilliermondii, Candida haemulonii, Candida holmii, Candida intermedia, Candida magnoliae, Candida maltosa, Candidamelinii, Candidaparapsilosis, Candidarugosa, Candida sonorensis, Candidatropicalis, Candidautilis, Candida versatilis, Cryptococcus albidus* var. *albidus, Debaryomyces hansenii* var. *fabryi, Debaryomyces hansenii, Debaryomyces marama, Debaryomycesnepalensis, Guilliermondellaselenospora, Hansenula glucozyma, Hansenula saturnus, Metschnikowia reukaufi, Pichia bovis, Pichia farinosa, Rhodotorula glutinis* var. *dairenensis, Rhodotorula graminis, Rhodotorula minuta, Rhodotorula rubra, Rhodosporidium diobovatum, Rhodosporidium sphaerocarpum, Rhodosporidium toruloides, Saccharomycopsis malanga, Schwanniomyces castellii, Sporidiobolus johnsonii, Sporobolomyces pararoseus, Sporobolomyces salmonicolor, Torulaspora delbrueckii* and *Yarrowia lipolytica* and so forth. Particularly preferred is *Candida magnoliae* IFO0705.

These microorganisms are generally obtainable from available or purchasable stock cultures. They may also be isolated from the natural world. The microorganisms having the ability of producing the enzyme mentioned above may be wild strains or mutants.

Alternatively, microorganisms derived by agenetic method such as cell fusion or gene manipulation may also be used as the microorganisms having an ability of producing the above-mentioned enzyme. Genetically engineered microorganisms having the ability of producing the enzyme can be obtained, for example, by a method comprising the step of isolating and/or purifying such enzyme and determining part or the whole of the amino acid sequence thereof, the step of obtaining a DNA sequence coding for the enzyme based on that amino acid sequence, the step of introducing this DNA into another microorganism to obtain a recombinant microorganism and the step of culturing this recombinant microorganism to obtain the enzyme in question (Japanese Patent Application Hei-11-345541).

For example, there may be mentioned transformant cells transformed with a plasmid containing a DNA coding for a carbonyl reducing enzyme derived from a microorganism belonging to the genus Candida and a DNA coding for an enzyme having the ability of regenerating a coenzyme on which the former enzyme is dependent. Preferably, there may be mentioned such transform ant cells in which the enzyme having the ability of regenerating said coenzyme is glucose dehydrogenase, such transform ant cells in which said glucose dehydrogenase is of the *Bacillus megaterium* origin, such transform ant cells in which the plasmid mentioned above is pNTCRG and such transform ant cells which are *Escherichia coli* cells. More preferably, there maybe mentioned *E. coli* HB101 (pNTCRG), accession number FERM-BP6898 [deposited with the Ministry of International Trade and Industry Agency of National Institute of Bioscience and Human Technology (1-3 Higashi 1-chome, Tsukuba City, Ibaraki Prefecture, Japan), deposited date: Sep. 28, 1999].

Any nutrient sources assimilable by such organisms can generally be used in cultivating such organisms. For example, carbon sources such as carbohydrates, e.g. glucose, sucrose and maltose, organic acids, e.g. lactic acid, acetic acid, citric acid and propionic acid, alcohols, e.g. ethanol and glycerol, hydrocarbons, e.g. paraffins, fats and oils such as soybean oil and rapeseed oil, and mixtures of these, and nitrogen sources such as ammonium sulfate, ammonium phosphate, urea, yeast extract, meat extract, peptone and corn steep liquor may be admixed. Furthermore, other inorganic salts, vitamins and like nutrients may also be incorporated in appropriate amounts as necessary.

The microorganisms can be cultivated under ordinary conditions in general use, for example aerobically at a pH of 4.0 to 9.5 in a temperature range of 20° C. to 45° C. for 10 to 96 hours. In cases where the substrate to be reduced is reacted with such a microorganism, the culture fluid of the above microorganisms can generally be submitted to the reaction as it is. A concentrate of the culture fluid may also be used. If a component in the culture fluid produces an adverse effect on the reaction, cells obtained by treating the culture fluid by centrifugation, for instance, or a product obtained by treating the cells is preferably used.

The above-mentioned product of treatment of microbial cells is not particularly restricted but mention may be made of, for example, dried cells obtained by dehydration using acetone or diphosphorus pentoxide or by drying utilizing a desiccator or fan, products of treatment with a surfactant, products of treatment with a bacteriolytic enzyme, immobilized cells or cell-free extract preparations obtained by disrupting cells, among others. Furthermore, an enzyme catalyzing the asymmetric reduction as purified from the culture may also be used.

In carrying out the reduction reaction, the substrate substituted acetylpyridine derivative may be added all at once in the beginning of the reaction or in divided portions as the reaction proceeds.

The reaction temperature is generally 10 to 60° C., preferably 20 to 40° C., and the pH during the reaction is 2.5 to 9, preferably 5 to 9.

The microorganism concentration in the reaction mixture may be selected appropriately depending on the ability thereof to reduce the substrate. The substrate concentration in the reaction mixture is preferably 0.01 to 50% (w/v), more preferably 0.1 to 30%.

The reaction is generally carried out with shaking or aeration and stirring. The reaction time may be selected according to the substrate concentration, microorganism concentration and other reaction conditions. Generally, the conditions are preferably selected so that the reaction may be complete in 2 to 168 hours.

For promoting the reduction reaction, such an energy source as glucose or ethanol is preferably added to the reaction mixture in an amount of 1 to 30%, whereby better results can be obtained. Further, by adding a coenzyme, such as reduced form nicotinamide adenine dinucleotide (NADH) or reduced form nicotinamide adenine dinucleotide phosphate (NADPH), which is generally required for reduction reactions using the biological method, it is also possible to promote the reaction. Specifically, such may be added directly to the reaction mixture or a reaction system having an ability of causing formation of NADH or NADPH may be added to the reaction mixture together with such a coenzyme in the oxide form. For example, the reaction system in which enzyme formate dehydrogenase reduces NAD to NADH on the occasion of its forming carbon dioxide and water from formic acid, or the reaction system in which glucose dehydrogenase reduces NAD or NADP to NADH or NADPH, respectively, on the occasion of its forming gluconolactone from glucose can be utilized.

It is also effective to add a surfactant, such as Triton (product of Nakalai Tesque), Span (product of Kanto Chemical) or Tween (product of Nakalai Tesque), to the reaction mixture. Further, for avoiding the inhibition of the reaction by an alcohol which is the substrate and/or the product of the reduction reaction, a water-insoluble organic solvent, such as ethyl acetate, butyl acetate, isopropyl ether or toluene, maybe added to the reaction mixture. For increasing the solubility of the substrate, it is also possible to add a water-soluble organic solvent such as methanol, ethanol, acetone, tetrahydrofuran or dimethyl sulfoxide.

The optically active hydroxyethyl derivative (10) produced by the reduction reaction is obtained by extracting the reaction mixture, directly or after separation of cells, with a solvent such as ethyl acetate or toluene and then removing the solvent. Further purification by recrystallization or silica gel column chromatography, for instance, gives a highly pure form of the optically active hydroxyethyl pyridine derivative.

When, on the other hand, hydrogen transfer type reduction is carried out as the enantioselective reduction, it is possible to reduce the substrate substituted acetylpyridine derivative either (R)- or (S)-selectively by selecting the catalyst to be used, whereby the corresponding (R)- or (S)-hydroxyethyl pyridine derivative can be obtained preferentially.

In carrying out the hydrogen transfer type reduction, it is necessary to prepare the catalyst prior to the reduction reaction. The catalyst to be used here is, for example, a catalyst prepared by mixing a ruthenium complex with an optically active amine and a base and such a catalyst can be prepared by the method described in Japanese Kokai Publication Hei-10-130289.

Bivalent ruthenium-arene complexes are preferred as the ruthenium complex and, among them, bis ($\eta^6$-benzene) diruthenium tetrachloride, bis($\eta$6-p-cymene) diruthenium tetrachloride and bis ($\eta^6$-mesitylene) diruthenium tetrachloride are particularly preferred.

Preferred as the optically active amine are optically active amine monosulfonates or optically active amino alcohols. Thus, mention may be made of 1,2-diphenylethylenediamine sulfonates, specifically
(S,S)-N-p-tosyl-1,2-diphenylethylenediamine,
(R,R)-N-p-tosyl-1,2-diphenylethylenediamine,
(S,S)-N-benzenesulfonyl-1,2-diphenylethylenediamine,
(R,R)-N-benzenesulfonyl-1,2-diphenylethylenediamine,
(S,S)-N-methanesulfonyl-1,2-diphenylethylenediamine,
(R,R)-N-methanesulfonyl-1,2-diphenylethylenediamine,
(S,S)-N-trifluoromethanesulfonyl-1,2-diphenylethylenediamine, (R,R)-N-trifluoromethanesulfonyl-1,2-diphenylethylenediamine and the like. In particular,
(S,S)-N-p-tosyl-1,2-diphenylethylenediamine or
(R,R)-N-p-tosyl-1,2-diphenylethylenediamine is more preferred.

The base to be used in preparing the catalyst is not particularly restricted but may be an ordinary organic or inorganic base, for example n-butyllithium, sodium hydride, potassium tert-butoxide, sodium ethoxide, sodium carbonate, potassium carbonate, sodium hydrogen carbonate, potassium hydrogen carbonate, sodium hydroxide, potassium hydroxide, calcium hydroxide, lithium hydroxide, barium hydroxide, magnesium hydroxide, sodium acetate, potassium acetate, ammonia, triethylamine, pyridine, piperidine, N,N-dimethylamino pyridine or the like. Preferred are sodium hydroxide and potassium hydroxide. The base may be added in the form of an aqueous solution.

For preparing the catalyst for hydrogen transfer type reduction, the above ruthenium complex, optically active amine and base are mixed together in an appropriate solvent in an arbitrary order. The ruthenium complex/optically active amine/base mixing mole ratio is basically 1:1:1 on the ruthenium basis. However, the optically active amine and the base may be used in excess. The solvent for use in preparing the catalyst is not particularly restricted but the same one as the solvent for use in carrying out the reduction reaction to be mentioned below is preferably used considering the efficiency in operation. The temperature in catalyst preparation is 0 to 100° C., preferably 15 to 60° C. The time required for catalyst preparation is about 1 to 10 hours. The catalyst prepared in the above manner is preferably submitted to the reduction reaction as it is in the solution form, but it is also possible to use the catalyst isolated from the solution by crystallization, for instance, in the reduction reaction. The use amount of the catalyst is 0.001 molar equivalent to 5 molar equivalents on the ruthenium basis relative to the substituted acetylpyridine derivative, which is the reduction substrate.

The hydrogen transfer type reduction reaction can be effected, for example, by admixing the catalyst prepared in the above manner with the substrate substituted acetylpyridine derivative and a hydrogen transfer source.

Usable as the hydrogen transfer source, namely the compound to serve as a hydrogen donor to the substrate, are isopropyl alcohol, benzhydrol, formic acid and formic acid salts, for instance, and isopropyl alcohol is preferred.

It is necessary to use the hydrogen transfer source in an amount of not less than 1 molar equivalent relative to the reduction substrate. Preferably, it is used in large excess, namely in an amount not less than 10 equivalents. When isopropyl alcohol is used as the hydrogen transfer source, this is preferably used as the solvent.

Any arbitrary solvent can be used as the reaction solvent. For example, there may be mentioned water; alcohol solvents such as methanol, ethanol, butanol, isopropyl alcohol, ethylene glycol and methoxy ethanol; amine solvents such as diethylamine, pyrrolidine and piperidine; hydrocarbon solvents such as benzene, toluene and cyclohexane; ether solvents such as diethyl ether, tetrahydrofuran, 1,4-dioxane, methyl tert-butyl ether and dimethoxyethane; ester solvents such as ethyl acetate and butyl acetate; ketone solvents such as acetone and methyl ethyl ketone; halogenated hydrocarbon solvents such as methylene chloride, chloroform and 1,1,1-trichloroethane; nitrogen-containing solvents such as dimethylformamide and acetonitrile; dimethyl sulfoxide, N-methylpyrrolidone, hexamethylphosphorotriamide and so on. Isopropyl alcohol is most preferred.

The reaction temperature is 0 to 150° C., preferably 15 to 60° C.

The end point of the reaction can be judged by analyzing the reaction mixture during reaction by thin layer chromatography, high performance liquid chromatography or gas chromatography, for instance, and detecting the decrease in the substrate substituted acetylpyridine derivative and the formation of the corresponding hydroxyethylpyridine derivative.

When a substituted acetylpyridine derivative represented by the general formula (12):

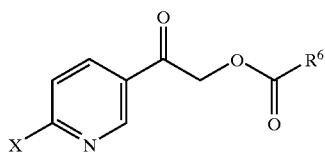

(12)

(in the formula, X represents a hydrogen, a halogen, a hydroxyl group, an acyloxy group containing 1 to 10 carbon atoms, an alkoxy group containing 1 to 10 carbon atoms, an amino group or a substituted amino group and R6 represents an alkyl group containing 1 to 15 carbon atoms, an aralkyl group containing 1 to 15 carbon atoms or an aryl group containing 6 to 16 carbon atoms) is used as the reduction substrate by hydrogen transfer reduction and the enantioselective reduction is carried out using isopropyl alcohol as the hydrogen transfer source, the corresponding optically active dihydroxyethylpyridine derivative represented by the general formula (14):

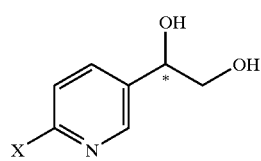

(14)

(in the formula, X is as defined above and * represents an asymmetric carbon atom) can be obtained directly if a base is caused to coexist in the reaction system.

The base to be caused to coexist for directly obtaining the optically active dihydroxy pyridine derivative is not particularly restricted but may be an inorganic or organic base, for example n-butyllithium, sodium hydride, potassium tert-butoxide, sodium ethoxide, sodium carbonate, potassium carbonate, sodium hydrogen carbonate, potassium hydrogen carbonate, sodium hydroxide, potassium hydroxide, calcium hydroxide, lithium hydroxide, barium hydroxide, magnesium hydroxide, sodium acetate, potassium acetate, ammonia, triethylamine, pyridine, piperidine, N,N-dimethylamino pyridine or the like. Sodium hydroxide or potassium hydroxide is preferred. From the operation efficiency viewpoint, it is preferred that the base is used in excess in the step of catalyst preparation so that the excess base may serve as the base for directly obtaining the optically active dihydroxypyridine derivative. The use amount of the base is preferably 0.1 to 10 molar equivalents relative to the substrate substituted acetylpyridine derivative. The base may be added in the form of an aqueous solution.

After completion of the reaction, the product can be obtained from the reaction mixture by a conventional after-treatment procedure. For example, water is added to the reaction mixture after completion of the reaction, followed by an extraction procedure using an ordinary extraction solvent such as ethyl acetate, diethyl ether, methylene chloride, toluene or hexane. From the extract obtained, the reaction solvent and extraction solvent are distilled off by heating under reduced pressure, for instance, whereupon the desired product can be obtained. Alternatively, after completion of the reaction, the reaction solvent may be immediately distilled off by heating under reduced pressure and the same procedure as above be then carried out. Although the thus-obtained product is nearly pure, its purity may further be improved by purification by conventional means such as purification by crystallization, fractional distillation or column chromatography.

In this step, the optically active hydroxyethyl pyridine derivative represented by the general formula (8) either in (R) or (S) form is obtained. The optically active hydroxyethyl pyridine derivatives which have the (R) absolute configuration are preferred, however.

3. Step (c)

This step (c) comprises treating an optically active hydroxyethyl pyridine derivative represented by the above general formula (15) with a base to give the corresponding optically active oxirane derivative represented by the above general formula (16).

The base to be used in this step (c) is an inorganic base or organic base. Specifically, the base includes, but is not limited to, metal hydroxides such as lithium hydroxide, sodium hydroxide, potassium hydroxide and calcium hydroxide; metal carbonates such as sodium carbonate, sodium hydrogen carbonate, potassium carbonate, potassium hydrogen carbonate and cesium carbonate; alkylmetals such as methyllithium, n-butyllithium, methylmagnesium bromide, i-propylmagnesium chloride and tert-butylmagnesium chloride; metal amides such as lithiumamide, sodium amide, lithium diIsopropylamide, magnesium diisopropylamide chloride, magnesiumdiisopropylamide bromide, magnesium dicyclohexylamide chloride; metal alkoxides such as sodium methoxide, magnesium ethoxide and potassium tert-butoxide; metal hydrides such as lithium hydride, sodium hydride, potassium hydride and calcium hydride; and amines such as triethylamine, ethyldiisopropylamine, N-methylpyrrolidine, dimethylaniline and pyridine. Preferred among them are metal hydroxides such as lithium hydroxide, sodium hydroxide, potassium hydroxide and calcium hydroxide and metal carbonates such as sodium carbonate, sodium hydrogen carbonate, potassium carbonate, potassium hydrogen carbonate and cesium carbonate.

The use amount of the base in the step (c) is 1 to 10 molar equivalents, preferably 1 to 3 molar equivalents, relative to the optically active hydroxyethyl pyridine derivative represented by the general formula (15).

The reaction solvent which can be used in the step (c) is water, an organic solvent, or a mixed solvent composed of water and an organic solvent. The above organic solvent is not particularly restricted but includes, among others, alcohol solvents such as methanol, ethanol, butanol, isopropyl alcohol, ethylene glycol and methoxyethanol; hydrocarbon solvents such as benzene, toluene and cyclohexane; ether solvents such as diethyl ether, tetrahydrofuran (THF), 1,4-dioxane, methyl t-butyl ether and dimethoxyethane; ester solvents such as ethyl acetate and butyl acetate; ketone solvents such as acetone and methyl ethyl ketone; halogenated solvents such as methylene chloride, chloroform and 1,1,1-trichloroethane; nitrogen-containing solvents such as dimethylformamide and acetonitrile; and aprotic polar solvents such as dimethyl sulfoxide, N-methylpyrrolidone and hexamethylphosphoric triamide. These may be used singly or two or more of them may be used in combination. Preferred are water, acetone, acetonitrile and tetrahydrofuran.

The step (c) is carried out at a reaction temperature of −50° C. to 100° C., preferably −20° C. to 30° C.

After completion of the reaction, the product is obtained from the reaction mixture by a conventional after-treatment procedure. For example, water is added to the reaction mixture after completion of the reaction, followed by an extraction procedure using an ordinary extraction solvent such as ethyl acetate, diethyl ether, methylene chloride, toluene or hexane. From the extract obtained, the reaction solvent and extraction solvent are distilled off by heating under reduced pressure, for instance, whereupon the desired product can be obtained. Alternatively, after completion of the reaction, the reaction solvent may be immediately distilled off by heating under reduced pressure and the same procedure as above be then carried out. Although the thus-obtained product is nearly pure, its purity may further be improved by purification by conventional means such as purification by crystallization, fractional distillation or column chromatography.

4. Step (d)

This step (d) comprises reacting the substituted acetylpyridine derivative represented by the general formula (7) as produced in the step (a) with a carboxylic acid represented by the general formula (11) in the presence of a base and a quaternary ammonium salt to prepare a substituted acetylpyridine derivative represented by the general formula (12).

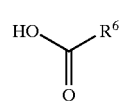

(11)

In the general formula (11), $R^6$ represents an alkyl group containing 1 to 15 carbon atoms, an aralkyl group containing 1 to 15 carbon atoms or an aryl group containing 6 to 16 carbon atoms. Specifically, it includes, but is not limited to, methyl, ethyl, n-propyl, i-propyl, n-butyl, i-butyl, tert-butyl, n-octyl, benzyl, anisyl, p-nitrobenzyl, phenyl, p-tolyl, naphthyl and the like. Methyl, ethyl, n-propyl, i-propyl, n-butyl, tert-butyl and phenyl are preferred and methyl, tert-butyl and phenyl are more preferred, and still more preferred is tert-butyl.

In this step (d), the use amount of a carboxylic acid (11) is preferably 1 to 5 molar equivalents, more preferably 1 to 3 molar equivalents, relative to the substituted acetylpyridine derivative of the general formula (7).

The base to be used in this step (d) may be any one having an ability of forming a salt with the carboxylic acid of general formula (11) and may be a conventional organic or inorganic base. Thus, it includes, but is not limited to, n-butyllithium, sodium hydride, potassium tert-butoxide, sodium ethoxide, sodium carbonate, potassium carbonate, sodium hydrogen carbonate, potassium hydrogen carbonate, sodium hydroxide, potassium hydroxide, calcium hydroxide, lithium hydroxide, barium hydroxide, magnesium hydroxide, triethylamine, pyridine, piperidine, N,N-dimethylamino pyridine and the like. Preferred are sodium hydrogen carbonate, sodium carbonate, potassium hydrogen carbonate and potassium carbonate.

In this step (d), the use amount of the base is preferably 1 to 5 molar equivalents, more preferably 1 to 3 molar equivalents, relative to the substituted acetylpyridine derivative of the general formula (7).

Instead of adding the above carboxylic acid and base respectively to the reaction system in this step (d), a salt separately prepared in advance by mixing the carboxylic acid and base together may be added. The salt separately prepared in advance by mixing the carboxylic acid and base together is the sodium or potassium salt of the carboxylic acid, for instance, which specifically includes sodium acetate, potassium acetate, sodium pivalate, potassium pivalate, sodium benzoate, potassium benzoate and the like.

The quaternary ammonium salt to be used in this step (d) is not particularly restricted provided that it is commercially and readily available. For example, there may be mentioned quaternary ammonium halides, quaternary ammonium hydroxides, quaternary ammonium sulfates, quaternary ammonium acetates and the like and, specifically, tetra(n-butyl)ammonium chloride, tetra(n-butyl)ammoniumbromide, tetra(n-butyl) ammonium iodide, tetra (n-butyl)ammonium hydroxide, tetra(n-butyl) ammonium hydrogen sulfate, tetra(n-butyl)ammonium acetate, tetramethylammonium chloride, tetramethylammonium bromide, benzyltrimethy lammonium chloride, benzyltrimethylammonium bromide and the like. Preferred are tetra(n-butyl) ammonium chloride and tetra(n-butyl)ammonium bromide.

In this step (d), the use amount of the quaternary ammonium salt is preferably 0.1 to 2 molar equivalents, more preferably 0.05 to 0.2 molar equivalent, relative to the substituted acetylpyridine derivative of the general formula (7).

In carrying out the reaction of step (d), various organic solvents can be used as the reaction solvents. As the organic solvents, there may be mentioned, among others, hydrocarbon solvents such as benzene, toluene and cyclohexane; ether solvents such as diethyl ether, tetrahydrofuran, 1,4-dioxane, methyl tert-butyl ether and dimethoxyethane; ester solvents such as ethyl acetate and butyl acetate; halogenated solvents such as methylene chloride, chloroform and 1,1,1-trichloroethane; nitrogen-containing solvents such as N,N-dimethylformamide, acetamide, formamide and acetonitrile; and aprotic polar solvents such as dimethyl sulfoxide, N-methylpyrrolidone and hexamethylphosphoric triamide. The above organic solvents may be used singly or two or more of them may be used in combination. Preferred are ether solvents such as diethyl ether, tetrahydrofuran, 1,4-dioxane, methyl tert-butyl ether and dimethoxyethane. Tetrahydrofuran is more preferred.

The reaction temperature is preferably 0° C. to 150° C., more preferably 20° C. to 80° C.

After completion of the reaction in this step (d), the product is obtained from the reaction mixture by a conventional after-treatment procedure. For example, a small amount of water is added, followed by an extraction procedure using an ordinary extraction solvent such as ethyl acetate, diethyl ether, methylene chloride, toluene or hexane. From the extract obtained, the reaction solvent and extraction solvent are distilled off by heating under reduced pressure, for instance, whereupon the desired product can be obtained. Although the thus-obtained product is nearly pure, its purity may further be improved by purification by conventional means such as purification by crystallization, fractional distillation or column chromatography.

5. Step (e)

In this step (e), an optically active dihydroxyethylpyridine derivative represented by the general formula (14) is produced by subjecting an optically active acyloxyhydroxyethylpyridine derivative represented by the general formula

(13) among the optically active hydroxyethyl pyridine derivatives obtainable in the step (b) to solvolysis.

The solvolysis in this step (e) is carried out in water or a protic organic solvent, or amixed solvent composed of water and a protic or aprotic organic solvent. The above protic organic solvent includes, among others, lower alcohol solvents such as methanol, ethanol, butanol, isopropyl alcohol, ethylene glycol and methoxyethanol; amine solvents such as diethylamine, pyrrolidine and piperidine; and so on. The above aprotic organic solvent includes hydrocarbon solvents such as benzene, toluene and cyclohexane; ether solvents such as diethyl ether, tetrahydrofuran, 1,4-dioxane, methyl t-butyl ether and dimethoxyethane; ester solvents such as ethyl acetate and butyl acetate; ketone solvents such as acetone and methyl ethyl ketone; halogen-containing solvents such as methylene chloride, chloroform and 1,1,1-trichloroethane; nitrogen-containing solvents such as dimethylformamide and acetonitrile; aprotic polar solvents such as dimethyl sulfoxide, N-methylpyrrolidone and hexamethylphosphoric triamide. Water and lower alcohols are preferred and lower alcohols are more preferred. Particularly preferred is methanol.

The solvolys is in this step (e) may be accelerated by adding a base. The base usable in the solvolys is includes inorganic or organic bases, e.g. sodium carbonate, potassium carbonate, sodiumhydrogen carbonate, potassium hydrogen carbonate, sodium hydroxide, potassium hydroxide, calcium hydroxide, lithium hydroxide, barium hydroxide, magnesium hydroxide, sodium acetate, potassium acetate, ammonia, triethylamine, piperidine, N,N-dimethylamino pyridine, tetra (n-butyl) ammonium hydroxide, tetramethylammonium hydroxide, benzyltrimethylammonium hydroxide and the like. Among them, quaternary ammonium hydroxides such as tetra(n-butyl)ammonium hydroxide, tetramethylammonium hydroxide and benzyltrimethylammonium hydroxide are preferred as the base, and tetra(n-butyl) ammonium hydroxide is more preferred.

In that case, the use amount Qf the base is 0.001 to 5 equivalents, preferably 0.01 to 1.0 equivalent, relative to the optically active acyloxyhydroxyethylpyridine derivative.

The reaction temperature in the step (e) is $-20°$ C. to $100°$ C., preferably $-10°$ C. to $50°$ C.

After completion of the reaction, the product can be obtained from the reaction mixture by a conventional after-treatment procedure. For example, water is added to the reaction mixture after completion of the reaction, followed by an extraction procedure using an ordinary extraction solvent such as ethyl acetate, diethyl ether, methylene chloride, toluene or hexane. From the extract obtained, the reaction solvent and extraction solvent are distilled off by heating under reduced pressure, for instance, whereupon the desired product can be obtained. Alternatively, after completion of the reaction, the reaction solvent may be immediately distilled off by heating under reduced pressure and the same procedure as above be then carried out. Although the thus-obtained product is nearly pure, its purity may further be improved by purification by conventional means such as purification by crystallization, fractional distillation or column chromatography.

In cases where the product has high solubility in water but has very low solubility in organic solvents, it is difficult to obtain the desired product by the ordinary reaction procedure such as mentioned above. In such cases, the solvolysis reaction is carried out in a lower alcohol solvent using a quaternary ammonium hydroxide as the base and, after completion of the solvolys is reaction, a low-polarity solvent is added to the reaction mixture to thereby cause the desired product to precipitate out, and by filtering the same, the desired product can be obtained with high purity and good efficiency by a simple procedure. The lower alcohol solvent and quaternary ammonium hydroxide to be used here are as mentioned herein above. The low-polarity solvent is a solvent low in polarity, inclusive of nonpolar solvents. It is not particularly restricted but may be any of those in which the optically active dihydroxyethylpyridine (14) is hardly soluble and which can mix with the solvolys is reaction solvent. When an alcohol solvent is used as the solvolys is reaction solvent, a hydrocarbon solvent is preferred as the low-polarity solvent, for example, n-hexane, n-pentane, benzene, toluene, xylene, petroleum ether, petroleum benzine and the like. Toluene is more preferred.

Among the substituted acetylpyridine derivatives represented by the general formula (9) as mentioned above, those substituted acetylpyridine derivatives represented by the general formula (1) which have an amino group at position 2 of the pyridine ring are novel compounds for which no process has been known in the art for the production thereof and which can now be produced by the process of the present invention [step (a) and, if necessary, a subsequent substitution reaction]. These derivatives are very useful in the production of intermediates of optically active beta-3 adrenaline receptor agonists.

In the above general formula (1), $R^1$ and $R^2$ each represents a hydrogen, an alkyl group containing 1 to 10 carbon atoms, an aralkyl group containing 1 to 10 carbon atoms, an acyl group containing 1 to 10 carbon atoms or an alkyloxy-carbonyl group containing 1 to 10 carbon atoms. $R^1$ and $R^2$ may be the same or different. Preferred is the case in which $R^1$ represents an acetyl group and $R^2$ a hydrogen. $Y^1$ is the same as that $Y^1$ described herein above referring to the general formula (9).

In the production method of a optically active dihydroxyethylpyridine derivative according to the invention described herein above, the pivaloyloxyacetylpyridine derivatives represented by the general formula (2) and the optically active pivaloyloxyhydroxyethylpyridine derivatives represented by the general formula (3) are useful intermediates improved in compound stability and handleability owing to the introduction of the pivaloyl group. Furthermore, these are novel compounds for which no process for their production has been known in the art and which can be produced by the process of the present invention. X appearing in the general formula (2) and (3) is the same as that X described herein above referring to the general formula (6).

Among the dihydroxyethylpyridine derivatives which can be produced for the first time according to the present invention, the compound represented by the formula (4) is a novel compound the use of which as a β-3 receptor agonist intermediate has been described by the present inventors.

BEST MODES FOR CARRYING OUT THE INVENTION

The following examples illustrate the present invention in further detail. They are, however, by no means limitative of the scope of the invention.

EXAMPLE 1

N1-[5-(2-chloroacetyl) pyridin-2-yl]ethanamide

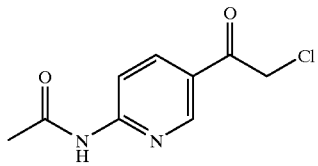

Sodium chloroacetate (5.2 g, 0.045 mol) and 4.3 g (0.045 mol) of magnesium chloride were added to a solution of 5.8 g (0.030 mol) of methyl 6-(methylcarboxamido)pyridine-3-carboxylate in 100 ml of THF, and the mixture was stirred at room temperature for 3 hours. Magnesium diisopropylamide chloride solution [solution prepared by adding 20 ml (0.144mol) of diisopropylamine drop wise at 40° C. to 67 ml (0.120 mol) of a 1.8 M/kg n-butylmagnesium chloride solution in THF, followed by 3 hours of stirring at 40° C. ] was added drop wise to this solution at 0° C. over 30 minutes, and the mixture was stirred at room temperature for 27 hours. A solution prepared by dissolving 25 ml (0.300 mol) of concentrated hydrochloric acid in 50 ml of water was added drop wise to the reaction mixture at 0° C. The resulting mixture was extracted with ethylacetate, and the or ganicphase was washed with a saturated aqueous solution of sodium hydrogen carbonate aqueous solution and dried over sodium sulfate. The solvent was distilled off under reduced pressure and the product was isolated and purified by silica gel column chromatography (hexane:ethyl acetate=1:1) to give 4.5 g (yield 71%) of the desired N1-[5-(2-chloroacetyl) pyridin-2-yl]ethanamide. $^1$H-NMR (400 MHz, DMSO-$d_6$) δ 10.93 (1H, s), 8.90 (1H, s), 8.29 (1H, d, J=8.8 Hz), 8.19 (1H, d, J=8.8 Hz), 5.16 (2H, s), 2.13 (3H, s). $^{13}$C-NMR (100 MHz, DMSO-$d_6$) δ 189.7, 170.1, 155.4, 149.4, 138.4, 125.6, 112.5, 47.4, 24.1. IR (KBr) 1690 cm$^{-1}$.

EXAMPLE 2

6-(Methylcarboxamido)-3-[2-(phenylcarbonyloxy) acetyl] pyridine

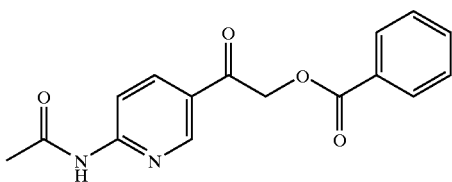

Sodium benzoate (144mg, 1.0 mmol) and 322 mg (1.0 mmol) of tetrabutylammonium bromide were added to a solution of 106 mg (0.5mmol) of N1-[5- (2-chloroacetyl) pyridin-2-yl]ethanamide in 5 ml of THF at room temperature, and the mixture was refluxed for 3 hours. The reaction mixture was suction-filtered, and the filtrate was extracted with ethylacetate. The organic phase was washed with a saturated aqueous solution of sodium hydrogen carbonate aqueous solution and then dried over sodium sulfate. The solvent was distilled off under reduced pressure and the product was isolated and purified by silica gel column chromatography (hexane:ethyl acetate=1:1) to give 128mg (yield 86%) of the desired 6-(methylcarboxamido)-3-[2-(phenylcarbonyloxy)acetyl]pyridine.

$^1$H-NMR (400 MHz, DMSO-$d_6$) δ 10.96 (1H, s), 8.96 (1H, d, J=2.5 Hz), 8.33 (1H, dd, J=8.8 Hz, 1.9 Hz), 8.22 (1H, d, J=8.8 Hz), 8.03 (1H, d, J=7.8 Hz), 7.70 (1H, t, J=7.2 Hz), 7.57 (2H, dd, J=7.6 Hz), 5.73 (2H, s), 2.15 (3H, s). $^{13}$C-NMR (100 MHz, DMSO-$d_6$) δ 191.0, 170.1, 165.3, 155.6, 149.0, 138.0, 133.8, 129.4, 129.1, 128.9, 125.2, 112.6, 66.9, 24.1. IR (KBr) 1720, 1700, 1690 cm$^{-1}$.

EXAMPLE 3

2-[6-(Methylcarboxamido) pyridin-3-yl]-2-oxoethyl ethanoate

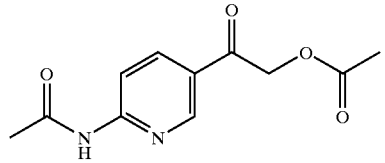

Sodium acetate (82 mg, 1.0 mmol) and 322 mg (1.0 mmol) of tetrabutylammonium bromide were added to a solution of 106 mg (0.5 mmol) of N1-[5- (2-chloroacetyl) pyridin-2-yl]ethanamide in 5 ml of THF at room temperature, and the mixture was refluxed for 2 hours. The reaction mixture was suction-filtered, and the filtrate was extracted with ethyl acetate. The organicphase was washed with a saturated aqueous solution of sodium hydrogen carbonate aqueous solution and then dried over sodium sulfate. The solvent was distilled off under reduced pressure and the product was isolated and purified by silica gel column chromatography (hexane:ethyl acetate- 1:1) to give 110 mg (yield 93%) of the desired 2-[6-(methylcarboxamido)pyridin-3-yl]-2-oxoethyl ethanoate. $^1$H-NMR (400 MHz, DMSO-$d_6$) δ 10.93 (1H, s), 8.89 (1H, d, J=2.4 Hz), 8.28 (1H, dd, J=8.8 Hz, 2.0 Hz), 8.19 (1H, d, J=8.8 Hz), 5.43 (2H, s), 2.14 (3H, s), 2.13 (3H, s) $^3$C-NMR (100 MHz, DMSO-$d_6$) δ 191.1, 170.2, 170.1, 155.6, 148.9, 138.0, 125.3, 112.6, 66.3, 24.2, 20.4. IR (KBr) 1750, 1710, 1690 cm$^{-1}$.

EXAMPLE 4

N1-[5-(2-Hydroxyacetyl) pyridin-2-yl]ethanamide

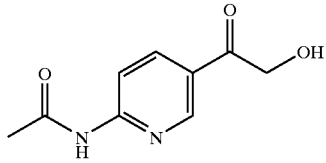

Potassium carbonate (3 mg, 0.02 mmol) was added to a solution of 48 mg (0.20 mmol) of 2-[6-(methylcarboxamido) pyridin-3-yl]-2-oxoethyl ethanoate in 5 ml of methanol, and the mixture was stirred at room temperature for 2 hours. The reaction mixture was extracted with ethyl acetate, the extract was dried over sodium sulfate, the solvent was then distilled off under reduced pressure, and the product was isolated and purified by silica gel column chromatography (hexane:ethyl acetate=1:1) to give 18 mg (yield 45%) of the desired N1-[5-(2-hydroxyacetyl)pyridin-2-yl]ethanamide.

$^1$H-NMR (400 MHz, DMSO-$d_6$) δ 10.86 (1H, s), 8.85 (1H, d, J=3.4 Hz), 8.24 (1H, dd, J=4.4 Hz, 2.0 Hz), 8.18 (1H, d, J=6.4 Hz), 5.20 (1H, d, J=5.4 Hz), 4.75 (2H, d, J=5.3 Hz), 2.12 (3H, s). $^{13}$C-NMR (100 MHz, DMSO-$d_6$) δ197.5, 170.1, 155.2, 148.7, 137.9, 125.9, 112.6, 65.4, 24.2.

EXAMPLE 5

2-[6-(Methylcarboxamido)pyridin-3-yl]-2-oxoethyl 2,2-dimethylpropanoate

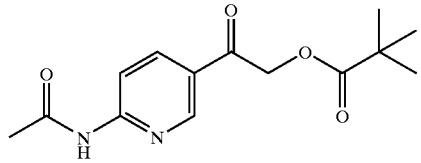

Pivalic acid (3.8 g, 38 mmol), 4.7 g (56 mmol) of sodium hydrogen carbonate and 0.61 g (1.9 mmol) of tetrabutylammonium bromide were added to a solution of 4.0 g (19 mmol) of N1-[5- (2-chloroacetyl)pyridin-2-yl]ethanamide in 70 ml of THF at room temperature, and the mixture was refluxed for 2 hours. Water (100ml) was added to the reaction mixture and the resulting mixture was extracted three times with 100 ml of ethyl acetate. The organic layer was washed with a saturated sodium hydrogen carbonate aqueous solution and then dried over sodium sulfate. The solvent was distilled off under reduced pressure and the product was isolated and purified by silica gel column chromatography (hexane:ethyl acetate 1:1) to give 4.2 g (yield 79%) of the desired 2-[6-(methylcarboxamido) pyridin-3-yl]-2-oxoethyl 2,2-dimethylpropanoate.

$^1$H-NMR (400 MHz, CDCl$_3$) δ 8.81 (1H, s), 8.32 (1H, d, J=8.6 Hz), 8.20 (1H, dd, J=8.8 Hz, 1.9 Hz), 8.10 (1H, s), 5.24 (2H, s), 2.25 (3H, s), 1.30 (9H, s). $^{13}$C-NMR (100 MHz, CDCl$_3$) δ 190.3, 178.1, 169.0, 154.8, 148.5, 138.0, 126.1, 113.2, 65.6, 38.8, 27.1, 24.8.

EXAMPLE 6

2-Oxo-2-pyridin-3-ylethyl 2, 2-dimethylpropanoate

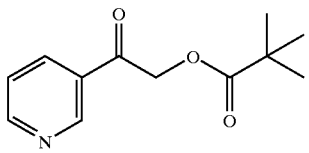

Pivalic acid (5.3 g, 52 mmol), 8.8 g (104 mmol) of sodium hydrogen carbonate and 0.84 g (2.6 mmol) of tetrabutylammonium bromide were added to a solution of 5.0 g (26 mmol) of 3- (2-chloroacetyl) pyridine hydrochloride in 80 ml of THF at room temperature, and the mixture was refluxed for 2 hours. Water (100 ml) was added to the reaction mixture and the resulting mixture was extracted three times with 100 ml of ethyl acetate. The organic layer was washed with a saturated sodium hydrogen carbonate aqueous solution and then dried over sodium sulfate. The solvent was distilled off under reduced pressure and the product was isolated and purified by silica gel column chromatography (hexane:ethyl acetate=1:1) to give 5.3 g (yield 92%) of the desired 2-oxo-2-pyridin-3-ylethyl 2,2-dimethylpropanoate.

$^1$H-NMR (400 MHz, DMSO-d$_6$) δ 9.13 (1H, s), 8.84 (1H, d, J=4.4 Hz), 8.29 (1H, d, J=7.8 Hz), 7.59 (1H, dd, J=7.8 Hz, 4.9 Hz), 5.50 (2H, s), 1.22 (9H, s). $^{13}$C-NMR (100 MHz, DMSO-d$_6$) δ 192.8, 177.0, 154.0, 149.0, 135.3, 129.5, 124.0, 66.4, 27.0, 26.9. IR (KBr) 1740, 1700 cm$^{-1}$.

EXAMPLE 7

Optically Active N1-[5-(2-Chloro-1-hydroxyethyl) pyridin-2-yl]ethanamide

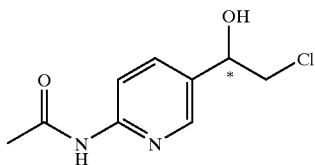

*Candida haltrus*(IFO 1941) was seeded in 30 ml of a semisynthetic medium (40 g glucose, 3 g yeast extract, 0.7 g KH$_2$PO$_4$, 1.3 g (NH$_4$)$_2$HPO$_4$, 0.8 g MgSO$_4$.7H$_2$O, 0.06 g ZnSO$_4$.7H$_2$O, 0.09 g FeSO$_4$.7H$_2$O, 0.005 g CuSO$_4$.7H$_2$O, 0.01 g MnSO$_4$, 0.1 g NaCl, 5 g CaCO$_3$,1 liter water, pH=6.8) as sterilized in a 500 ml Sakaguchi flask and shake-cultured aerobically at 30° C. for 2 days. To the culture fluid were added 300 mg of N1-[5-(2-chloroacetyl)pyridin-2-yl] ethanamide and 1.2 g of glucose, and the reaction was carried out at 30° C. with stirring for 48 hours. After completion of the reaction, the reaction mixture was extracted with ethyl acetate, and the extract was concentrated under reduced pressure to give a concentrate containing the product. The concentrate was purifiedona silica gel column (hexane:ethyl acetate=1/1) to give optically active N1-[5-(2-chloro-1-hydroxyethyl) pyridin-2-yl]ethanamide.

Upon HPLC analysis [column: Chiralcel AS (product of Daicel Chemical Industries), eluent: hexane/isopropanol=80/20, flow rate: 1 ml/min, temperature: 40° C., detection wavelength: 210 nm], the optical purity was 98% ee.

1H-NMR (400 MHz, DMSO-d$_6$) δ10.46 (1H, s), 8.29 (1H, s), 8.01 (1H, d, J=8.3 Hz), 7.76 (1H, d, J=8.8 Hz), 5.90 (1H, t, J=4.4 Hz), 4.82–4.79 (1H, m), 3.79–3.74 (2H, m), 2.07 (3H, s). $^{13}$C-NMR (100 MHz, DMSO-d$_6$) δ169.5, 151.6, 146.3, 136.4, 132.8, 112.9, 70.2, 49.9, 24.0. IR (KBr) 3440, 1660 cm$^{-1}$. $[α]_D^{22}$: +0.032 (C=1.00, in acetone)

EXAMPLE 8

Optically Active N1-[5-(2-Chloro-1-hydroxyethyl) pyridin-2-yl]ethanamide

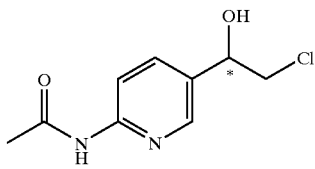

*Rhodotorula rubra* (IFO 0383) was seeded in 30 ml of a semisynthetic medium (40 g glucose, 3 g yeast extract, 0.7 g KH$_2$PO$_4$, 1.3 g (NH$_4$)$_2$HPO$_4$, 0.8 g MgSO$_4$.7H$_2$O, 0.06g ZnSO$_4$.7H$_2$O, 0.09 g FeSO$_4$.7H$_2$O, 0.005 g CuSO$_4$.7H$_2$O, 0.01 g MnSO$_4$, 0.1 g NaCl, 5 g CaCO$_3$,1 liter water, pH=6.8) as sterilized in a500 ml Sakaguchi flask and shake-cultured aerobically at 30° C. for 2 days. To the culture fluid were added 300 mg of N1-[5-(2-chloroacetyl)pyridin-2-yl] ethanamide and 1.2 g of glucose, and the reaction was carried out at 30° C. with stirring for 48 hours. After completion of the reaction, the reaction mixture was extracted with ethyl acetate, and the extract was concentrated under reduced pressure to give a concentrate containing the product. The concentrate was purified on a silica gel column (hexane:ethyl acetate=1/1) to give optically active N1-[5-(2-chloro-1-hydroxyethyl) pyridin-2-yl]ethanamide.

Upon HPLC analysis [column: Chiralcel AS (product of Daicel Chemical Industries), eluent: hexane/isopropanol= 80/20, flow rate: 1 ml/min, temperature: 40° C., detection wavelength: 210 nm], the optical purity was 98% ee. $[\alpha]_D^{22}$: −0.035 (C=1.00, in acetone)

EXAMPLE 9

Optically Active 2-Hydroxy-2-[6-(methylcarboxamido) pyridin-3-yl]ethyl 2,2-dimethylpropanoate

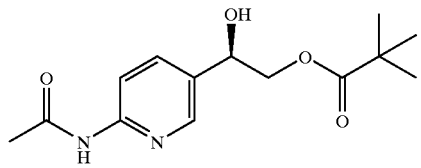

Each yeast strain was seeded in 30 ml of a semisynthetic medium(40g glucose, 3g yeast extract, 1g $KH_2PO_4$, 6.5g $(NH_4)_2HPO_4$, 0.8 g $MgSO_4.7H_2O$, 0.06 g $ZnSO_4.7H_2O$, 0.09 g $FeSO_4.7H_2O$, 0.005 g $CuSO_4.7H_2O$, 0.01 g $MnSO_4$, 0.1 g NaCl, 5 g $CaCO_3$,1 liter water, pH=6.8) as sterilized in a 500 ml Sakaguchi flask and shake-cultured aerobically at 30° C. for 2 days. One milliliter of the culture fluid obtained, 5 mg of 2-[6-(methylcarboxamido)pyridin-3-yl]-2-oxoethyl 2,2-dimethylpropanoate and 40 mg of glucose were added into a medium-sized test tube, and shake reaction was carried out at 30° C. for 1 day. After completion of the reaction, the reaction mixture was extracted with ethyl acetate, and the extract was concentrated under reduced pressure to give 2-hydroxy-2-[6-(methylcarboxamido) pyridin-3-yl]ethyl 2, 2-dimethylpropanoate as a crude product. The conversion rate was determined by analyzing the crude product by HPLC (column: Develosil ODS-HG-3 (product of Nomura Chemical), eluent: acetonitrile/0.1% $KH_2PO_4$=25/75, flow rate: 1.0 ml/min, column temperature: 40° C., detection wavelength: 210nm) and the optical purity was determined by purifying the crude product by thin layer chromatography, followed by HPLC analysis (column: Chiralcel OJ (product of Daicel Chemical Industries), eluent: hexane/isopropanol=90/10, flow rate: 1 ml/min, column temperature: 40° C., detection wavelength: 210 nm). The results thus obtained are shown below in Table 1.

TABLE 1

| Microorganism | | Conversion % | Optical purity % ee | Absolute configuration |
|---|---|---|---|---|
| Ashbya gossypii | IFO 0560 | 96 | 99 | R |
| Candida catenulata | IFO 0731 | 64 | 98 | R |
| Candida fructus | IFO 1581 | 42 | 72 | R |
| Candida galacta | IFO 10031 | 66 | 61 | R |
| Candida gropengiesseri | IFO 0659 | 34 | 90 | R |
| Candida guilliermondii | IFO 0454 | 75 | 93 | R |
| Candida haemulonii | IFO 10001 | 66 | 93 | R |
| Candida holmii | IFO 0660 | 57 | 73 | R |
| Candida intermedia | IFO 0761 | 64 | 91 | R |
| Candida magnoliae | IFO 0705 | 81 | 77 | R |
| Candida maltosa | IFO 1975 | 78 | 81 | R |

TABLE 1-continued

| Microorganism | | Conversion % | Optical purity % ee | Absolute configuration |
|---|---|---|---|---|
| Candida melinii | IFO 0747 | 57 | 95 | R |
| Candida parapsilosis | IFO 0585 | 64 | 78 | R |
| Candida rugosa | IFO 0750 | 52 | 81 | R |
| Candida sonorensis | IFO 10027 | 59 | 69 | R |
| Candida tropicalis | IFO 1404 | 62 | 61 | R |
| Candida utilis | IFO 0639 | 63 | 100 | R |
| Candida versatillis | IFO 1941 | 54 | 100 | R |
| Cryptococcus albidus var. albidas | IFO 0378 | 54 | 83 | R |
| Debaryomyces hansenii var. fabryi | IFO 0015 | 60 | 95 | R |
| Debaryomyces hansenii | IFO 0082 | 84 | 89 | R |
| Debaryomyces marama | IFO 0668 | 74 | 97 | R |
| Debaryomyces nepalensis | IFO 0039 | 22 | 88 | R |
| Guilliermondella selenospora | IFO 1850 | 71 | 69 | R |
| Hansenula glucozyma | IFO 1472 | 45 | 63 | R |
| Hansenula saturnus | IFO 0809 | 84 | 97 | R |
| Metschnikowia reukaufii | IFO 0749 | 76 | 69 | R |
| Pichia bovis | IFO 1886 | 68 | 92 | R |
| Pichia farinosa | IFO 0463 | 86 | 92 | R |
| Rhodotorula glutinis var. dairenensis | IFO 0415 | 96 | 100 | R |
| Rhodotorula graminis | IFO 0190 | 45 | 95 | R |
| Rhodotorula minuta | IFO 0928 | 39 | 73 | R |
| Rhodotorula rubra | IFO 0383 | 73 | 94 | R |
| Rhodsporidium diobovatum | IFO 0688 | 56 | 94 | R |
| Rhodsporidium sphaerocarpum | IFO 1438 | 64 | 96 | R |
| Rhodsporidium toruloides | IFO 0413 | 64 | 94 | R |
| Saccharomycopsis malanga | IFO 1710 | 48 | 74 | R |
| Schwanniomyces castellii | IFO 1840 | 44 | 73 | R |
| Sporidiobolus johnsonii | IFO 6903 | 73 | 99 | R |
| Sporobolomyces pararoseus | IFO 0471 | 45 | 84 | R |
| Sporobolomyces salmonicolor | IAM 12249 | 41 | 83 | R |
| Torulaspora delbrueckii | IFO 0381 | 41 | 62 | R |
| Yarrowia lipolytica | IFO 1548 | 97 | 99 | R |

2-Hydroxy-2-[6-(methylcarboxamido)pyridin-3-yl]ethyl 2,2-dimethylpropanoate $^1$H-NMR (400 MHz, $CDCl_3$) δ10.46 (1H, s), 8.26 (1H, d, J=2.5 Hz), 8.02 (1H, d, J=8.3 Hz), 7.73 (1H, dd, J=8.8 Hz, 2.5 Hz), 5.66 (1H, d, J=4.4 Hz), 4.78 (1H, dd, J=10.7 Hz, 5.9 Hz), 4.15 (1H, dd, J=10.7 Hz, 5.9 Hz), 4.03 (1H, dd, J=11.6 Hz, 5.4 Hz), 2.06 (3H, s), 1.05 (9H, s). $^{13}$C-NMR (100 MHz, $CDCl_3$) δ177.1, 169.2, 151.4, 146.1, 136.2, 132.7, 112.6, 68.0, 67.8, 67.8, 38.2, 26.8, 23.8.

EXAMPLE 10

Optically Active Hydroxyethyl pyridine Derivatives

Each yeast strain was seeded in 30 ml of a semisynthetic medium (40g glucose, 3g yeast extract, 1g $KH_2PO_4$, 6.5g $(NH_4)_2HPO_4$, 0 0.8 g $MgSO_4.7H_2O$, 0.06 g $ZnSO_4.7H_2O$, 0.09 g $FeSO_4.7H_2O$, 0.005 g $CuSO_4.7H_2O$, 0.01 g $MnSO_4$, 0.1 g NaCl, 5 g $CaCO_3$,1 liter water, pH=6.8) as sterilized in a 500-ml Sakaguchi flask and shake-cultured aerobically at 30° C. for 2 days. One milliliter of the culture fluid obtained, 5 mg of each substituted acetylpyridine derivative represented by the general formula (9) and 40 mg of glucose were added to a medium-sized test tube, and shake reaction was carried out at 30° C. for 1 day. After completion of the reaction, the reaction mixture was extracted with ethyl acetate, and the extract was concentrated under reduced pressure to give a crude product. The conversion rate was determined by analyzing the crude product by HPLC (column: Develosil ODS-HG-3 (product of Nomura Chemical), eluent: acetonitrile/water=25/75, flow rate: 1.0 ml/min, column temperature: 40° C., detection wavelength: 210nm) and the optical purity was determined by purifying the crude product by thin layer chromatography, followed by HPLC analysis (column: Chiralcel OJ (product of Daicel Chemical Induxtries), eluent: hexane/isopropanol=95/5, flow rate: 1 ml/min, temperature: 40° C., detection wavelength: 210 nm). The results thus obtained are shown below in Table 2.

g of (R)-2-chloro-1-pyridin-3-ylethan-1-ol hydrochloride as white crystals. The optical purity was 99.7% ee.

$^1$H-NMR (400 MHz, CD$_3$OD) δ 8.93 (d, 1H), δ8.84 (dd, 1H), δ8.72 (d, 1H), δ8.10 (dd, 1H), δ5.23 (m, 1H), δ3.88 (m, 2H)

TABLE 2

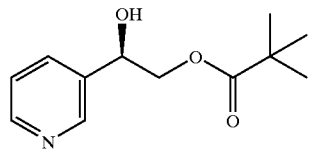

| Microorganism | | | Substrate (9) X | Y$^1$ | Conversion % | Optical purity %** | Absolute configuration |
|---|---|---|---|---|---|---|---|
| Candida | intermedia | IFO 0761 | AcNH | Cl | 56 | 78 | R |
| Candida | tropicalis | IFO 1404 | AcNH | Cl | 44 | 87 | R |
| Cryptococcus | albidus var. albidas | IFO 0378 | AcNH | Cl | 20 | 84 | R |
| Rhodotorula | graminis | IFO 0190 | AcNH | Cl | 48 | 87 | R |
| Rhodotorula | rubra | IFO 0383 | AcNH | Cl | 67 | 98 | R |
| Sporidiobolus | johnsonii | IFO 8903 | AcNH | Cl | 84 | 91 | R |
| Schwanniomyces | castellii | IFO 1840 | H | Cl | 47 | 61 | R |
| Candida | magnolise | IFO 0705 | H | OCOtBu | 100 | 71 | R |
| Sporidiobolus | johnsonii | IFO 6903 | H | OCOtBu | 70 | 66 | R |

EXAMPLE 11

(R)-2-Chloro-1-pyridin-3-ylethan-1-ol

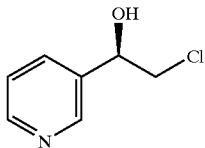

The recombinant *Escherichia coli* HB101 (pNTCRG), accession number FERM BP-6898, was seeded in 100 ml of a semisynthetic medium (15 g glycerol, 3 g of yeast extract, 6 g Na$_2$HPO$_4$,3 g KH$_2$PO$_4$, 2 g NaCl, 0.5 g MgSO$_4$.7H$_2$O, 1 liter water, pH=7.2) as sterilized in a 500 ml Sakaguchi flask and shake-cultured at 37° C. for 28 hours. 2-chloro-1-pyridin-3-ylethan-1-one hydrochloride (2 g) was suspended in 8 ml of phosphate buffer, and the suspension was adjusted to pH=5.5 with 5 N NaOH. Then, 40 ml of the above culture fluid, 0.04 ml of Triton X-100, 2.8 g of glucose and 2.3 mg of NADP were added, and the reaction was carried at 30° C. with stirring for 7 hours. After completion of the reaction, the reaction mixture was extracted with ethyl acetate, the extract was concentrated under reduced pressure, and was purified on a silica gel column (hexane:ethylacetate=1:2) to give 1.04g of (R)-2-chloro-1-pyridin-3-ylethan-1-ol as a transparent oil. The optical purity was determined by the same method as used in EXAMPLE 10 and was 97.1% ee.

$^1$H-NMR (400 MHz, CD$_3$OD) δ8.58 (d, 1H), δ8.46 (dd, 1H), δ7.90 (d, 1H), δ7.44 (dd, 1H), δ4.93 (m, 1H), δ3.75 (m, 2H).

The thus-obtained (R)-2-chloro-1-pyridin-3-ylethan-1-ol was dissolved in a methanolic hydrochloric acid solution, methyl tert-butyl ether was then gradually added drop wise, and the mixture was stirred at room temperature for 1 hour. The resulting white precipitate was filtered off to give 1.04

EXAMPLE 12

(R)-2-Hydroxy-2-pyridin-3-ylethyl 2,2-dimethylpropanoate

2-Oxo-2-pyridin-3-ylethyl 2,2-dimethylpropanoate (2 g), 2.8 g of glucose, 2.3 mg of NADP and 0.02 ml of Triton X×100 were added to 20 ml of the same culture fluid as used in Example 11, and the reaction was carried at 30° C. with stirring for 2 hours while adjusting the pH to 6.5 with a 5 N aqueous sodium hydroxide solution. After completion of the reaction, the reaction mixture was extracted with ethyl acetate, and the 30 extract was concentrated under reduced pressure to give 2.1 g of (R)-2-hydroxy-2-pyridin-3-ylethyl 2,2-dimethylpropanoate as a light-yellow oil. The optical purity was determined by the same method as used in EXAMPLE 10 and was 100% ee.

$^1$H-NMR (400 MHz, DMSO-d$_6$) δ8.57 (1H, s), 8.48 (1H, d, J=4.9 Hz), 7.78 (1H, d, J=6.9 Hz), 7.37 (1H, dd, J=7.6 Hz, 4.6 Hz), 5.77 (1H, s), 4.86 (1H, t, J=5.4 Hz), 4.20 (1H, dd, J=11.0 Hz, 6.1 Hz), 4.08 (1H, dd, J=11.3 Hz, 5.4 Hz), 1.05 (9H, s). $^{13}$C-NMR (100 MHz, DMSO-d$_6$) δ177.1, 148.6, 148.0, 137.4, 134.1, 123.3, 68.3, 67.9, 38.2, 26.8. IR (KBr) 3200, 1730 cm$^{-1}$. $[\alpha]_D^{25}$: −22.87 (c=1, MeOH)

EXAMPLE 13

(R)-2-Hydroxy-2-[6-(methylcarboxamido)-pyridin-3-yl]ethyl ethanoate

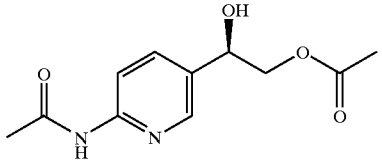

Bis (η⁶-mesitylene)diruthenium tetrachloride (3.10 mg, 0.0053 mmol), 7.73 mg (0.021 mmol) of (S,S)-N-p-tosyl-1,2-diphenylethylenediamine and 50 mg (0.212 mmol) of the 2-[6-(methylcarboxamido) pyridin-3-yl]-2-oxoethyl ethanoate obtained by the method of EXAMPLE 3 were mixed together in 5.5 ml of isopropyl alcohol, the mixture was stirred in an argon atmosphere at 80° C. for 20 minutes, cooled to 0° C., and 0.053 ml of a 1 M potassium hydroxide/isopropyl alcohol solution was added. The resulting solution was further stirred at 0° C. for 2 hours and then at 15 to 20° C. for 18 hours. Water was added to the reaction mixture, and the resulting mixture was extracted with ethyl acetate. The organic layer was dried over anhydrous magnesium sulfate, the solvent was distilled off under reduced pressure, and the residue obtained was purified by silica gel column chromatography to give 36.8 mg (yield 73%) of (R)-2-hydroxy-2-[6-(methylcarboxamido) pyridin-3-yl]ethyl ethanoate. The optical purity was determined by the same method as used in EXAMPLE 9 and was 89.7% ee.

$^1$H-NMR (400 MHz, CDCl$_3$) δ 9.14 (1H, bs), 8.27 (1H, s), 8.20 (1H, d), 7.74 (1H, dd), 4.97 (1H, dd), 4.28 (1H, dd), 4.17 (1H, dd), 2.86 (1H, bs), 2.21 (3H, s), 2.11 (3H, s), 1.69 (1H, bs).

EXAMPLE 14

Optically Active N1-(5-Oxiran-2-ylpyridin-2-yl)ethanamide

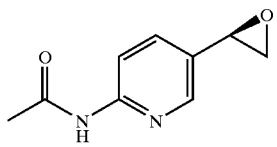

To a solution of 107 mg (0.50 mmol) of optically active N1-[5-(2-chloro-1-hydroxyethyl)pyridin-2-yl]ethanamide in 5 ml of acetone was added 0.5ml (0.50mmol) of 1 N sodium hydroxide at 0° C., and the mixture was stirred at 0° C. for 2 hours. Cold water was added to the reaction mixture, the resulting mixture was extracted with ethyl acetate, the extract was dried over sodium sulfate, the solvent was distilled off under reduced pressure, and the product was isolated and purified by silica gel column chromatography (hexane/ethyl acetate=1/1) to give 82 mg (yield 92%) of the desired product, optically active N1-(5-oxiran-2-ylpyridin-2-yl)ethanamide.

$^1$H-NMR (400 MHz, CDCl$_3$) δ 8.47 (1H, br), 8.21 (1H, s), 8.20 (1H, d, J=12.2 Hz), 7.56 (1H, dd, J=8.8 Hz, 1.7 Hz), 3.86 (1H, s), 3.17 (1H, dd, J=4.4 Hz), 2.83 (1H, dd, J=4.9 Hz, 2.0 Hz), 2.20 (3H, s).

EXAMPLE 15

(R)-N1-[5-(1,2-Dihydroxyethyl) pyridih-2-yl]ethanamide

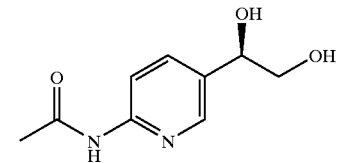

The (R)-2-hydroxy-2-[6-(methylcarboxamido)-pyridin-3-yl]ethyl 2,2-dimethylpropanoate (1.50 g, 5.35 mmol, 100% ee) obtained by the method of EXAMPLE 9 was dissolved in 15 ml of methanol, 0.5 ml of a 1 M tetra(n-butyl) ammonium hydroxide/methanol solution was added, and the mixture was stirred at 20° C. for 4 hours. To this solution was added 30 ml of toluene, and the mixture was stirred at −20° C. for 3 hours. The crystallized precipitate was filtered off, washed with toluene and dried at 40° C. and 1 Torr for 6 hours to give 0.937 g (89% yield) of (R)-N1-(5-(1,2-dihydroxyethyl) pyridin-2-yl]ethanamide as white crystals.

$^1$H-NMR (400 MHz, DMSO-d$_6$) δ 10.43 (1H, s), 8.22 (1H, d, J=2.0 Hz), 8.00 (1H, d, J=8.3 Hz), 7.69 (1H, dd, J=8.3, 2.0 Hz), 5.31 (1H, d, J=3.9Hz), 4.74–4.77 (1H, m), 4.51–4.53 (1H, m), 3.33–3.59 (2H, m), 2.07 (3H, s)

EXAMPLE 16

(R)-1-Pyridin-3-ylethane-1,2-diol hydrochloride

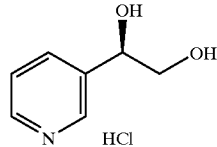

The 2-hydroxy-2-pyridin-3-ylethyl 2,2-dimethylpropanoate concentrate (2 g) obtained in Example 12 was dissolved in a methanolic hydrochloric acid solution, and the solution was refluxed for 48 hours and then concentrated under reduced pressure. The concentrate was redissolved in methanol, methyl-t-butyl ether was gradually added drop wise, and the resulting mixture was stirred at room temperature for 1 hour. The resulting white precipitate was filtered off to give 1.31 g of (R)-1-pyridin-3-ylethane-1,2-diol hydrochloride as white crystals.

$^1$H-NMR (400 MHz, CD$_3$OD) δ 8.79 (d, 1H), δ 8.70 (d, 1H), δ 6 8.60 (d, 1H), δ 8.00 (dd, 1H), δ 4.87 (m, 1H), 67 3.68 (m, 2H). [α]$_D^{25}$: −20.99 (c=1, MeOH)

EXAMPLE 17

(R)-1-Pyridin-3-ylethane-1,2-diol

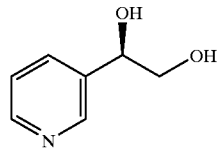

The 2-hydroxy-2-pyridin-3-ylethyl 2, 2-dimethylpropanoate concentrate (100mg) obtained in Example 12 was dissolved in 1 ml of methanol, 50 μl of a 1 M methanolic Bu₄NHOH was added, and the reaction was carried at room temperature for3 hours. The reaction mixture was concentrated under reduced pressure and the concentrate was purified on a silica gel column (ethyl acetate:methanol=4:1) to give 50 mg of (R)-1-pyridyl-3-ylethane-1,2-diol as a light-yellow oil.

¹H-NMR (400 MHz, CD₃OD) δ 8.79 (d, 1H), δ8.70 (d, 1H), δ8.60 (d, 1H), δ 8.00 (dd, 1H), δ 4.87 (m, 1H), δ 3.68 (m, 2H)

EXAMPLE 18

(R)-N1-[5-(1,2-Dihydroxyethyl) pyridin-2-yl] ethanamide

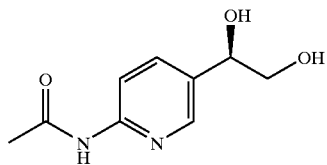

Bis (η⁶-mesitylene)diruthenium tetrachloride (3.10 mg, 0.0053 mmol), 7.73 mg (0.021 mmol) of (S,S)-N-p-tosyl-1,2-diphenylethylenediamine and 50 mg (0.212 mmol) of the 2- [6- (methylcarboxamido)pyridin-3-yl]-2-oxoethyl ethanoate obtained by the method of EXAMPLE 3 were mixed together in 5.5 ml of isopropyl alcohol, the mixture was stirred in an argon atmosphere at 80° C. for 20 minutes, cooled to 0° C. and, 0.27 ml of a 1 M potassium hydroxide/isopropyl alcohol solution was added. The resulting solution was further stirred at 0° C. for 6hours, 10ml of toluene was then added, and the resulting crystals was filtered off under reduced pressure. The crystals were washed with cold isopropyl alcohol and dried under vacuum (40° C., 1 torr, 6 hours) to give 20.8 mg (yield 50%) of (R)-N1-[5-(1,2-dihydroxyethyl)pyridin-2-yl]ethanamide with an optical purity of 90.6% ee.

The optical purity of the product obtained in this example was determined by derivatizing the vicinal diol moiety of the product into the acetonide by treatment with 2,2-dimethoxypropane and p-toluenesulfonic acid in acetone and subjecting the derivative to HPLC analysis (column: Chiralcel OJ (product of Daicel Chemical Industries), eluent: hexane/isopropanol=90/10, flow rate: 1 ml/min, temperature: 40° C., detection wavelength: 210 nm)

INDUSTRIAL APPLICABILITY

The invention, which has the constitution mentioned above, makes it possible to produce optically active dihydroxyethylpyridine derivatives and optically active oxirane derivatives, which are intermediates of beta3 adrenaline receptor agonists, from readily available raw materials in a safe and efficient manner and in an industrially advantageous manner.

What is claimed is:

1. A production method of an optically active hydroxyethyl pyridine derivative represented by the general formula (10):

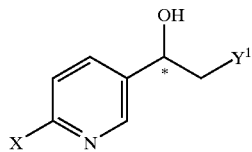

in the formula, X represents a hydrogen, a halogen, a hydroxyl group, an acyloxy group containing 1 to 10 carbon atoms, an alkoxy group containing 1 to 10 carbon atoms, an amino group or a substituted amino group, Y¹ represents a halogen, a hydroxyl group, an acyloxy group containing 1 to 10 carbon atoms, a sulfonyloxy group containing 1 to 10 carbon atoms, an alkoxy group containing 1 to 10 carbon atoms, an amino group, an alkylamino group containing 1 to 15 carbon atoms, an aralkylamino group containing 1 to 15 carbon atoms, a sulfanyl group, an alkyl sulfanyl group containing 1 to 10 carbon atoms or anaralkyl sulfanyl group containing 1 to 10 carbon atoms and * represents an asymmetric carbon atom, which comprises using a microorganism-derived carbonyl reducing enzyme or a culture of a microorganism having an ability of producing said carbonyl reducing enzyme or a treatment product thereof to thereby (R)-selectively reduce a substituted acetylpyridine derivative represented by the general formula (9):

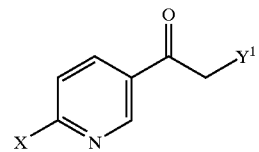

in the formula, X and Y₁ are as defined above.

2. The production method according to claim 1, wherein Y¹ represents a chlorine.

3. The production method according to claim 1, wherein X represents any of a hydrogen, a chlorine and an acetylamino group.

4. The production method according to claim 1, wherein the microorganism having an ability of producing the carbonyl reducing enzyme is a microorganism belonging to the genus Ashbya, Candida Cryptococcus, Debaryomyces, Guilliermondella, Hansenula Metschnikowia, Pichia, Rhodotorula, Rhodosporidium, Saccharomycopsis, Schwanniomyces, Sporidiobolus, Sporobolomyces, Torulaspora or Yarrowia.

5. The production method according to claim 4, wherein the microorganism having an ability of producing the carbonyl reducing enzyme is a microorganism selected from the group consisting of *Ashbya gossypii, Candida catinulata, Candida fructus, Candida galacta, Candida gropengiesseri, Candida guilliermondii, Candida haemulonii, Candida holmii, Candida intermedia, Candidamagnoliae, Candidamaltosa, Candida melinii, Candida parapsilosis, Candida rugosa, Candida sonorensis, Candida tropicalis, Candida utilis, Candida versatilis, Cryptococcus albidus* var. albidus, *Debaryomyces hansenii* var. fabryi, *Debaryomyces hansenii, Debaryomyces marama, Debaryomycesnepalensis, Guilliermondella selenospora, Hansenula glucozyma, Hansenula saturnus, Metschnikowia reukaufi, Pichia bovis, Pichia farinosa, Rhodotorula glutinis* var. dairenensis, *Rhodotorula graminis, Rhodotorula minuta, Rhodotorula rubra, Rho-*

*dosporidium diobovatum, Rhodosporidium sphaerocarpum, Rhodosporidium toruloides, Saccharomycopsis malanga, Schwanniomyces castellii, Sporidiobolus johnsonii, Sporobolomyces pararoseus, Sporobolomyces salmonicolor, Torulaspora delbrueckii* and *Yarrowia lipolytica*.

6. The production method according to claim 5, wherein the microorganism having an ability of producing the carbonyl reducing enzyme is *Candida magnoliae* IFO 0705.

7. The production method according to claim 1, wherein the microorganism having an ability of producing the carbonyl reducing enzyme is a transform ant cell transformed by a plasmid containing a DNA coding for the carbonyl reducing enzyme derived from a microorganism belonging to the genus Candida and a DNA coding for an enzyme having an ability of regenerating a coenzyme on which the former enzyme is dependent.

8. The production method according to claim 7, wherein the transform ant cell is *E. coli* HB10 (pNTCRG), accession number FERM-BP6898.

* * * * *